US009795764B2

(12) United States Patent
Pacheco et al.

(10) Patent No.: US 9,795,764 B2
(45) Date of Patent: Oct. 24, 2017

(54) REMOTE CATHETER POSITIONING SYSTEM WITH HOOP DRIVE ASSEMBLY

(71) Applicant: Catheter Precision, Inc., Ledgewood, NJ (US)

(72) Inventors: Robert Pacheco, Bayside, NY (US); Steve Foley, Kerrville, TX (US); David Jenkins, Budd Lake, NJ (US); Thomas Jackson, Cambridge (GB); Luke Hares, Milton (GB); Daniel Leonard Fuller, Suffolk (GB)

(73) Assignee: CATHETER PRECISION, INC., Ledgewood, NJ (US)

( * ) Notice: Subject to any disclaimer, the term of this patent is extended or adjusted under 35 U.S.C. 154(b) by 385 days.

(21) Appl. No.: 14/494,752

(22) Filed: Sep. 24, 2014

(65) Prior Publication Data
US 2015/0094732 A1    Apr. 2, 2015

Related U.S. Application Data

(60) Provisional application No. 61/883,304, filed on Sep. 27, 2013.

(51) Int. Cl.
*A61M 25/01* (2006.01)
*A61B 17/00* (2006.01)
*A61B 34/30* (2016.01)

(52) U.S. Cl.
CPC ......... *A61M 25/0113* (2013.01); *A61B 34/30* (2016.02); *A61B 2017/00212* (2013.01); *A61B 2034/301* (2016.02)

(58) Field of Classification Search
CPC .................................... A61M 25/0113
USPC .................................... 318/560, 34
See application file for complete search history.

(56) References Cited

U.S. PATENT DOCUMENTS

| 4,549,538 A | 10/1985 | Schadrack, III et al. |
| 4,721,123 A | 1/1988 | Cosentino et al. |
| 5,226,892 A | 7/1993 | Boswell |
| 5,644,551 A | 7/1997 | Carmichael et al. |
| 5,649,956 A | 7/1997 | Jensen et al. |
| 5,682,890 A | 11/1997 | Kormos et al. |

(Continued)

FOREIGN PATENT DOCUMENTS

| JP | 2007527296 A | 9/2007 |
| WO | 2005087128 A1 | 9/2005 |

(Continued)

OTHER PUBLICATIONS

WIPO, International Preliminary Report on Patentability; PCT/US2006/027024; dated Jan. 16, 2008; 8pgs.

(Continued)

Primary Examiner — David S Luo
(74) Attorney, Agent, or Firm — The Marbury Law Group, PLLC

(57) ABSTRACT

Systems, methods, and devices of the various embodiments provide a hoop drive assembly. A hoop drive assembly according to the various embodiments may include one or more toothed rings and one or more motors coupled to the one or more toothed rings. In the various embodiments, rotation of the one or more toothed rings may change an orientation of a turret supported by the hoop drive assembly and/or move a control actuator of a catheter held in a modular plate coupled to the turret.

25 Claims, 17 Drawing Sheets

(56) References Cited

U.S. PATENT DOCUMENTS

| | | |
|---|---|---|
| 5,810,880 A | 9/1998 | Jensen et al. |
| 5,814,038 A | 9/1998 | Jensen et al. |
| 5,855,583 A | 1/1999 | Wang et al. |
| 6,007,550 A | 12/1999 | Wang et al. |
| 6,063,095 A | 5/2000 | Wang et al. |
| 6,080,181 A | 6/2000 | Jensen et al. |
| 6,096,004 A | 8/2000 | Meglan et al. |
| 6,132,368 A | 10/2000 | Cooper |
| 6,171,234 B1 | 1/2001 | White et al. |
| 6,171,277 B1 | 1/2001 | Ponzi |
| 6,200,315 B1 | 3/2001 | Gaiser et al. |
| 6,346,072 B1 | 2/2002 | Cooper |
| 6,396,232 B2 | 5/2002 | Haanpaa et al. |
| 6,398,755 B1 | 6/2002 | Belef et al. |
| 6,413,264 B1 | 7/2002 | Jensen et al. |
| 6,445,984 B1 | 9/2002 | Kellogg |
| 6,461,372 B1 | 10/2002 | Jensen et al. |
| 6,527,782 B2 | 3/2003 | Hogg et al. |
| 6,620,174 B2 | 9/2003 | Jensen et al. |
| 6,713,985 B2 * | 3/2004 | Aoshima ............ H02K 7/116 318/599 |
| 6,726,675 B1 | 4/2004 | Beyar |
| 6,788,999 B2 | 9/2004 | Green |
| 6,850,817 B1 | 2/2005 | Green |
| 6,963,792 B1 | 11/2005 | Green |
| 6,974,465 B2 | 12/2005 | Belef et al. |
| 6,999,852 B2 | 2/2006 | Green |
| 7,006,895 B2 | 2/2006 | Green |
| 7,090,683 B2 | 8/2006 | Brock et al. |
| 7,118,582 B1 | 10/2006 | Wang et al. |
| 7,169,141 B2 | 1/2007 | Brock et al. |
| 7,204,844 B2 | 4/2007 | Jensen et al. |
| 7,214,230 B2 | 5/2007 | Brock et al. |
| 7,276,044 B2 | 10/2007 | Ferry et al. |
| 7,314,230 B2 | 1/2008 | Kumagai et al. |
| 7,331,967 B2 | 2/2008 | Lee et al. |
| 7,357,774 B2 | 4/2008 | Cooper |
| 7,371,210 B2 | 5/2008 | Brock et al. |
| 7,377,906 B2 | 5/2008 | Selkee |
| 7,537,570 B2 | 5/2009 | Kastelein |
| 7,630,752 B2 | 12/2009 | Viswanathan |
| 7,648,513 B2 | 1/2010 | Green et al. |
| 7,758,564 B2 | 7/2010 | Long et al. |
| 8,046,049 B2 | 10/2011 | Govari et al. |
| 8,672,880 B2 | 3/2014 | Cohen et al. |
| 2001/0053879 A1 | 12/2001 | Mills et al. |
| 2002/0042620 A1 | 4/2002 | Julian et al. |
| 2002/0072704 A1 | 6/2002 | Mansouri-Ruiz |
| 2002/0120254 A1 | 8/2002 | Julian et al. |
| 2002/0177789 A1 | 11/2002 | Ferry et al. |
| 2002/0183723 A1 | 12/2002 | Belef et al. |
| 2004/0077942 A1 | 4/2004 | Hall et al. |
| 2004/0254566 A1 | 12/2004 | Plicchi et al. |
| 2005/0038412 A1 | 2/2005 | Rabiner et al. |
| 2005/0065435 A1 | 3/2005 | Rauch et al. |
| 2005/0113719 A1 | 5/2005 | Saadat |
| 2005/0203382 A1 | 9/2005 | Govari et al. |
| 2005/0209614 A1 | 9/2005 | Fenter et al. |
| 2005/0222554 A1 | 10/2005 | Wallace et al. |
| 2005/0228440 A1 | 10/2005 | Brock et al. |
| 2005/0277874 A1 | 12/2005 | Selkee |
| 2005/0283140 A1 | 12/2005 | Jensen et al. |
| 2006/0009735 A1 | 1/2006 | Viswanathan et al. |
| 2006/0041181 A1 | 2/2006 | Viswanathan et al. |
| 2006/0084911 A1 | 4/2006 | Belef et al. |
| 2006/0084945 A1 | 4/2006 | Moll et al. |
| 2006/0095022 A1 | 5/2006 | Moll et al. |
| 2006/0161136 A1 | 7/2006 | Anderson et al. |
| 2006/0161137 A1 | 7/2006 | Orban et al. |
| 2006/0161138 A1 | 7/2006 | Orban et al. |
| 2006/0167441 A1 | 7/2006 | Wang et al. |
| 2006/0178559 A1 | 8/2006 | Kumar et al. |
| 2006/0229587 A1 | 10/2006 | Beyar |
| 2006/0235436 A1 | 10/2006 | Anderson et al. |
| 2006/0270915 A1 | 11/2006 | Ritter et al. |
| 2006/0293643 A1 | 12/2006 | Wallace et al. |
| 2007/0012135 A1 | 1/2007 | Tierney et al. |
| 2007/0016174 A1 | 1/2007 | Millman et al. |
| 2007/0019330 A1 | 1/2007 | Wolfersberger |
| 2007/0021776 A1 | 1/2007 | Jensen et al. |
| 2007/0043338 A1 | 2/2007 | Moll et al. |
| 2007/0043455 A1 | 2/2007 | Viswanathan et al. |
| 2007/0149946 A1 | 6/2007 | Viswanathan et al. |
| 2007/0233044 A1 | 10/2007 | Wallace et al. |
| 2007/0239172 A1 | 10/2007 | Lee et al. |
| 2007/0250073 A1 | 10/2007 | Brock et al. |
| 2007/0250074 A1 | 10/2007 | Brock et al. |
| 2007/0260115 A1 | 11/2007 | Brock et al. |
| 2007/0276423 A1 | 11/2007 | Green |
| 2007/0283263 A1 | 12/2007 | Zawde et al. |
| 2007/0299479 A1 | 12/2007 | Saksena |
| 2008/0009791 A1 | 1/2008 | Cohen et al. |
| 2008/0039869 A1 | 2/2008 | Mills et al. |
| 2008/0045892 A1 | 2/2008 | Ferry et al. |
| 2008/0059598 A1 | 3/2008 | Garibaldi et al. |
| 2008/0119824 A1 | 5/2008 | Weitzner et al. |
| 2008/0119872 A1 | 5/2008 | Brock et al. |
| 2008/0125793 A1 | 5/2008 | Brock et al. |
| 2008/0125794 A1 | 5/2008 | Brock et al. |
| 2008/0140087 A1 | 6/2008 | Barbagli |
| 2008/0147091 A1 | 6/2008 | Cooper |
| 2008/0183136 A1 | 7/2008 | Lenker et al. |
| 2008/0215065 A1 | 9/2008 | Wang et al. |
| 2008/0245946 A1 | 10/2008 | Yu |
| 2008/0249536 A1 | 10/2008 | Stahler et al. |
| 2008/0300592 A1 | 12/2008 | Weitzner et al. |
| 2009/0012533 A1 | 1/2009 | Barbagli et al. |
| 2009/0082722 A1 | 3/2009 | Munger et al. |
| 2009/0105639 A1 | 4/2009 | Weitzner et al. |
| 2009/0105645 A1 | 4/2009 | Kidd et al. |
| 2009/0248043 A1 | 10/2009 | Tierney et al. |
| 2010/0010475 A1 | 1/2010 | Teirstein et al. |
| 2010/0256558 A1 | 10/2010 | Olson et al. |
| 2011/0077590 A1 | 3/2011 | Plicchi et al. |
| 2012/0182134 A1 | 7/2012 | Doyle |
| 2012/0184955 A1 | 7/2012 | Pivotto et al. |
| 2012/0197182 A1 | 8/2012 | Millman et al. |
| 2012/0220931 A1 | 8/2012 | Cohen et al. |
| 2013/0138118 A1 | 5/2013 | Doyle |

FOREIGN PATENT DOCUMENTS

| | | |
|---|---|---|
| WO | 2007008967 A2 | 1/2007 |
| WO | 2009092059 A2 | 7/2009 |

OTHER PUBLICATIONS

State Intellectual Property Office of the People's Republic of China, First Office Action, dated Oct. 30, 2009, Chinese Patent Application 200680025512.7, "Remotely Controlled Catheter Insertion System," with English translation, (24 pgs. total).

Chinese Application 200680025512.7, State Intellectual Property Office of the People's Republic of China, Office Action dated Feb. 13, 2012.

Chinese Application 200980102420.8, State Intellectual Property Office of the People's Republic of China, Office Action dated Feb. 16, 2012.

International Preliminary Report on Patentability, Intl Application PCT/US2009/031357. International Bureau of WIPO, dated Jul. 29, 2010.

International Search Report and Written Opinion, Intl Application PCT/US2009/031357. International Search Authority, U.S. Patent and Trademark Office (ISA/US), dated Mar. 19, 2009.

U.S. Appl. No. 13/051,736, Final Office Action dated Nov. 5, 2012.

Hein et al., "Robot Supported Insertion of Catheters for Hyperthermia and Branch Therapy," Computer Assisted Radiology and Surgery, 1998, pp. 660-663.

Macoviak, "Catheter System for Surgical Access and Circulatory Support of the Heart," USPTO, Official Gazette, vol. 1278, Jan. 6, 2004.

(56) References Cited

OTHER PUBLICATIONS

U.S. Appl. No. 13/051,736, Non-Final Office Action dated Jul. 17, 2012.
U.S. Appl. No. 12/903,397, Non-Final Office Action dated Nov. 19, 2012.
Canadian Application 2,646,846, Office Action dated Sep. 19, 2012.
Extended European Search Report dated Apr. 17, 2013; European Application No. 09702983.9.
Japanese Patent Application No. 2010-543298; Office Action dated Mar. 19, 2013.
U.S. Appl. No. 13/461,463, Final Office Action dated Jun. 27, 2014.
U.S. Appl. No. 13/461,463, Non-Final Office Action dated Oct. 31, 2014.
U.S. Appl. No. 12/515,005, Non-Final Office Action dated Apr. 11, 2013.
U.S. Appl. No. 13/078,663, Non-Final Office Action dated Aug. 14, 2014.

* cited by examiner

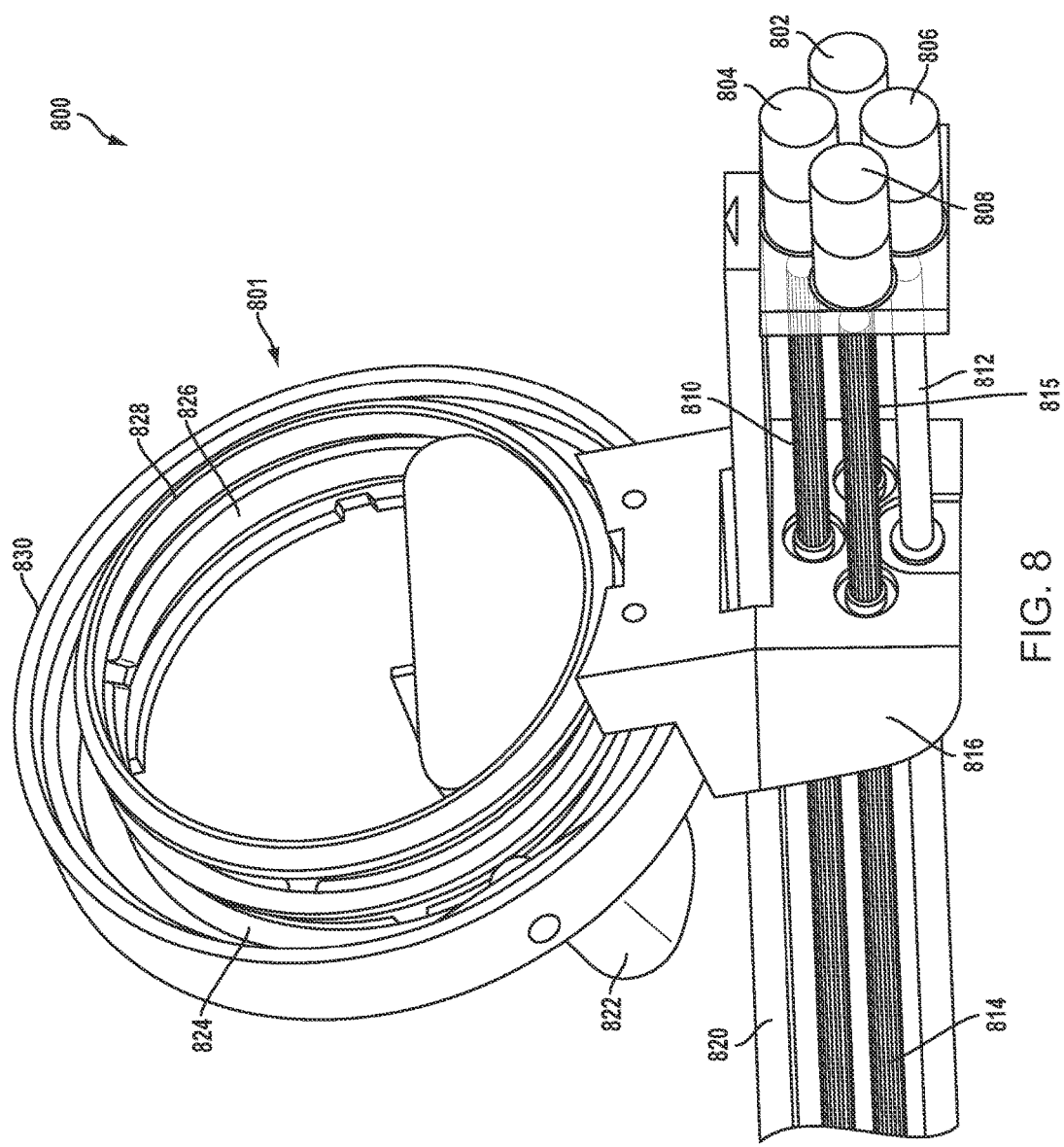

REMOTE CATHETER POSITIONING SYSTEM WITH HOOP DRIVE ASSEMBLY

CROSS REFERENCE TO RELATED APPLICATIONS

The present application claims the benefit of priority to U.S. Provisional Patent Application No. 61/883,304, entitled "REMOTE CATHETER POSITIONING SYSTEM WITH HOOP DRIVE ASSEMBLY," filed Sep. 27, 2013, the entire contents of which are incorporated herein by reference.

BACKGROUND

Many procedures involving catheter insertion, such as invasive electrophysiology procedures, rely on fluoroscopy or other radioactive imaging techniques to help navigate and position the catheter within a patient's body at a particular site, such as in the heart or inside a blood vessel in the circulatory system. High dosages of radiation can have long term adverse health effects. A patient may be directly exposed only once or twice to radiation during such procedures and avoid such adverse effects. However, physicians, medical technicians and staff can experience a large cumulative radiation dosage over time, both directly and indirectly, from conducting many procedures.

To protect the operator and staff from this radiation, shielding such as lead aprons, gowns, glasses, skirts, etc., is worn. Such lead clothing, especially a lead apron, is quite heavy and uncomfortable, and its use has been associated with cervical and lumbar spine injury.

SUMMARY OF THE INVENTION

Systems, methods, and devices of the various embodiments provide an improved drive mechanism for a remote catheter positioning system in the form of a hoop drive assembly. A hoop drive assembly for a remote catheter positioning system according to the various embodiments may include one or more toothed rings and one or more motors coupled to the one or more toothed rings. In the various embodiments, rotation of the one or more toothed rings may change an orientation of a turret of the remote catheter positioning system and/or move a control actuator of a catheter held in a modular plate coupled to the turret.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

FIG. 8 and FIG. 9 are cutaway perspective views of a catheter positioning system according to another embodiment.

DETAILED DESCRIPTION

Figure 1:
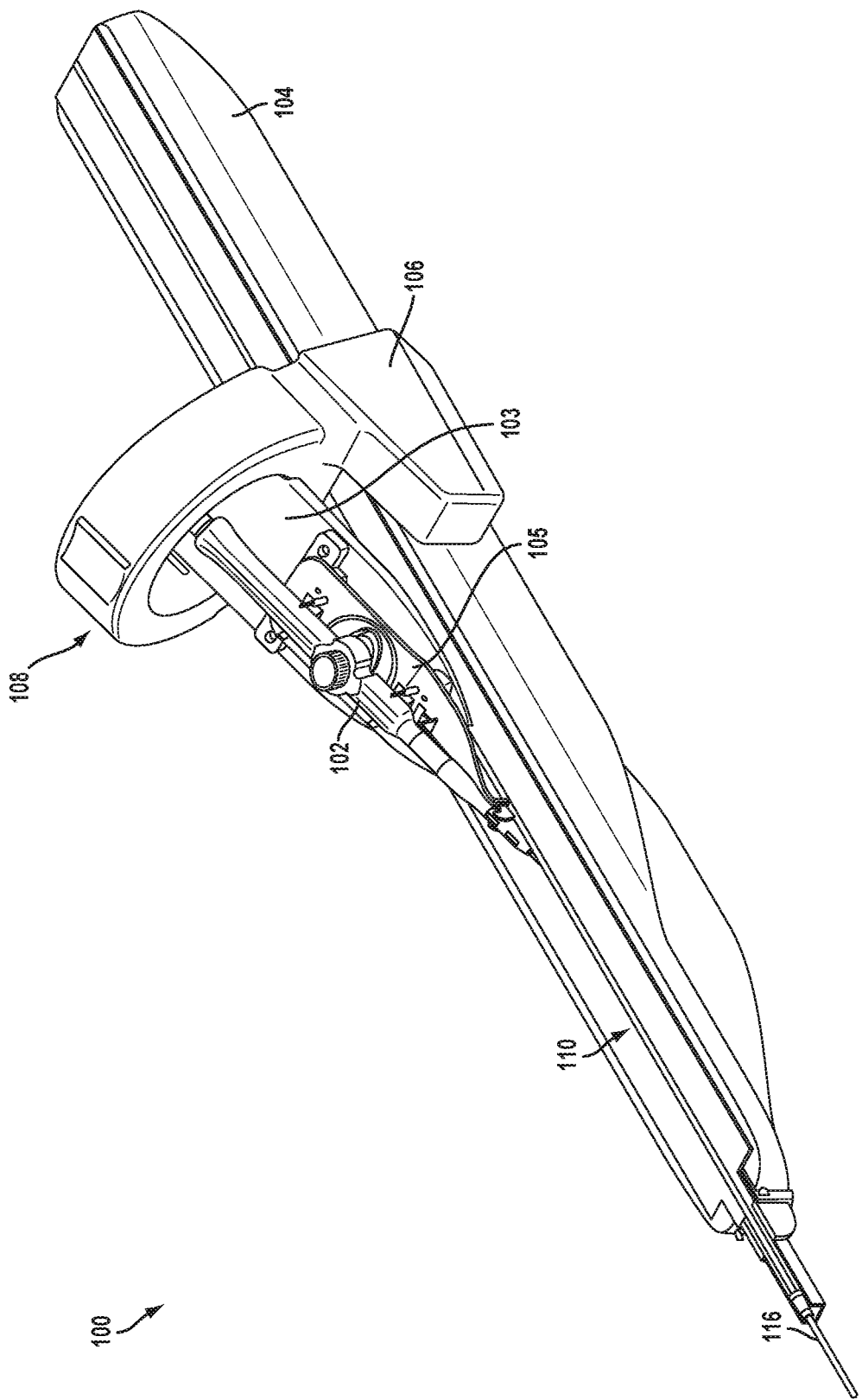
FIG. 1 is a perspective view of a catheter positioning system according to an embodiment.

Various embodiments will be described in detail with reference to the accompanying drawings. Wherever possible, the same reference numbers will be used throughout the drawings to refer to the same or like parts. References made to particular examples and implementations are for illustrative purposes and are not intended to limit the scope of the invention or the claims.

Systems, methods, and devices of the various embodiments provide hoop drive assemblies for use with catheter positioning systems. The hoop drive assemblies according to the various embodiments may include one or more toothed rings and one or more motors coupled to the one or more toothed rings. The one or more motors coupled to the one or more toothed rings may be any type of motors, such as servomotors, hydraulic motors, etc. An example servo motor may include a sensor providing position feedback to a servomotor controller. An example hydraulic motor may include a hydraulic motor suitable for use in magnetic resonance imaging (MRI) machines. In the various embodiments, rotation of the one or more toothed rings may change an orientation of a turret supported by the hoop drive assembly and/or move a control actuator of a catheter held in a modular plate coupled to the turret.

Hoop drive assemblies according to the various embodiments may enable the rotation of a turret supporting a catheter within a remote catheter positioning system and enable the actuation of catheter controls without requiring motors for catheter control actuation to be located in the turret. The hoop drive assemblies of the various embodiments enable motors for catheter control actuation to be located within the catheter positioning system remote from the turret supporting the catheter and/or remote from the hoop drive assembly itself. Locating the motors for catheter control actuation away from the turret supporting the catheter may enable the turret to rotate without having to break electrical and/or control connections for the motors across the path of rotation for the turret. Thus the embodiments eliminate the need for moving electrical contact, such as slip rings, commutators, or other rotary connections. Additionally, locating the motors for catheter control actuation remote from the turret supporting the catheter may reduce the weight needed to be supported in the turret, may enable the motors for catheter control actuation to be moved to areas having improved isolation or shielding from fluid connections to the catheter and/or patient bodily fluids (e.g., blood). Also, interference with catheter operations from the stray electromagnetic fields generated by the motors may be reduced or eliminated by positioning the motors for catheter control actuation away from the catheter and behind shielding. Positioning the drive motors in this manner may also reduce electrical currents that could be induced in a catheter by stray electromagnetic fields emitted by the motors.

In an embodiment, a catheter positioning system may include a linear rail (or rail assembly), a sled configured to move along the linear rail in response to an actuation of a sled motor, a hoop drive assembly coupled to the sled, a remote controller, and a system processor connected to the remote controller, sled motor, and hoop drive assembly. The system processor may be configured with processor-executable instructions to perform operations to activate the sled motor and/or one or more motors of the hoop drive assembly in response to an input from the remote controller.

In an embodiment, a hoop drive assembly may include three toothed rings aligned such that the first toothed ring, the second toothed ring, and the third toothed ring may rotate independently around a common axis of rotation. Inner teeth of the first toothed ring may interlock with drive teeth of a first gear drive rotationally coupled to a turret support within the second toothed ring. Rotation of the first toothed ring may rotate a drive shaft of the first gear drive. Inner teeth of the third toothed ring may interlock with drive teeth of a second gear drive rotationally coupled to the turret support within the second toothed ring. Rotation of the third toothed ring may rotate a drive shaft of the second gear drive. Rotation of the second toothed ring may change an orientation of the turret support, which in turn may rotate a turret coupled to the turret support. In an embodiment, the turret coupled to the turret support may include a first actuator driver that interfaces with the drive shaft of the first gear drive and a second actuator driver that interfaces with the drive shaft of the second gear drive. Rotation of the drive shaft of the first gear drive may move the first actuator driver and rotation of the drive shaft of the second gear drive may move the second actuator driver. In an embodiment, the hoop drive assembly may include a modular plate that may hold a catheter. The modular plate may include a first actuator that interfaces with the first actuator driver of the turret and a second actuator that interfaces with the second actuator driver of the turret. The first actuator of the modular plate may be configured to move a control actuator of the catheter held in the modular plate in response to actuation of the first actuator driver of the turret and the second actuator of the modular plate may be configured to move another control actuator of the catheter held in the modular plate in response to actuation of the second actuator driver of the turret.

In an embodiment, a toothed ring of a hoop drive assembly may be coupled to the motor driving the rotation of the toothed ring by a drive belt transferring the rotation of the motor to the toothed ring. In another embodiment, a toothed ring of a hoop drive assembly may be coupled to the motor driving the rotation of the toothed ring by a set of one or more drive gears. In an embodiment, the motors driving the toothed rings of the hoop drive assembly may be located in the hoop drive assembly or in the sled that the hoop drive assembly is connected to. In another embodiment, the motors driving the toothed rings of the hoop drive assembly may be located remote from the hoop drive assembly and the sled to which the hoop drive assembly is connected, and may rotate the toothed rings of the hoop drive assembly via drive shafts (e.g., flexible drive shafts).

In various embodiments, the catheter positioning system may communicate information from the turret of the hoop drive assembly to the system processor of the catheter positioning system. In an embodiment, the turret may include an inductive receiver and an optical transmitter connected to a processor of the turret. The sled of the catheter positioning system may include an inductive transmitter and an optical receiver. The inductive receiver of the turret may be aligned with the inductive transmitter on the sled (e.g., in a predetermined "parking position") so that inductive power may be provided to the turret processor from the inductive transmitter via the inductive receiver. Similarly, the optical transmitter of the turret may be aligned with an optical receiver on the sled so that data may be sent to the system processor from the turret processor via the optical transmitter and optical receiver. In another embodiment, the turret may include an inductive transceiver connected to the turret processor and the sled may include an inductive transceiver connected to the system processor. In this manner, power may be provided to the turret processor and data from the turret processor may be transmitted to the system processor via the inductive link between the turret inductive transceiver and the sled inductive transceiver. In a further embodiment, the inductive transmitter and/or inductive transceiver of the sled may be an inductive coil within a drive assembly enclosure encasing the hoop drive assembly, and the inductive coil may form an internal opening surrounding a portion of the turret including the turret inductive receiver and/or inductive transceiver. In this manner, power may be provided to the turret processor irrespective of an orientation of the turret within the drive assembly enclosure.

Various examples of hoop drive assemblies including three toothed rings are discussed herein. The discussions of hoop drive assemblies including three toothed rings are provided merely as examples to better illustrate the aspects of the various embodiments. Hoop drive assemblies may have less than three toothed rings, such as two or one toothed ring, or more than three toothed rings, such as four, five, or more toothed rings, without departing from the scope of the invention.

Any type of catheter may be suitable for use with the various embodiments. Example catheters that may be used in various embodiments may include a handle portion and tube portion. The handle portion may be located at a proximal end of the catheters while the distal end of the tube portion may be inserted into the body of a patient. The handle portion of example catheters may also include an irrigation port, which may be used to introduce water or other fluids to lubricate the catheters and ease insertion or retraction into the patient. The handle portion may also include a back port through which one or more wires or cables may leave the handle portion. The one or more wires or cables may supply power to the example catheters or transmit signals, such as sending commands from a remote controller or other control device to the catheters or relaying data from one or more transducers present on the example catheters. Example catheters may include controls (e.g., on the handle portion) that control the behavior of the catheters. An example control that may be included on a catheter include a front flange and rear flange that may be squeezed together such that this motion may move one or more mechanism at the tip of the catheter (e.g., extending or retracting a laser tip from inside a tube portion of the catheter). The laser tip may be retracted by pulling the front flange and rear flange apart. Other example controls that may be include on a catheter include controls for deflecting the tip of the catheter to ease navigation inside a patient and/or for controlling one or more transducers at the tip (e.g., electrical leads, one or more sensor devices, ultrasound devices, etc.). The various embodiments may be applicable to catheters with different types of controls.

FIG. 1 illustrates an embodiment catheter positioning system 100. The catheter positioning system 100 may include a linear rail 104 supporting a track 110 and a sled 106 configured to move along the track 110. The sled 106 may include a hoop drive assembly 108 configured to support a turret 103 and catheter handle/catheter 102 coupled to a modular plate 105. In an embodiment, the modular plate 105 may include mechanisms to support and hold the catheter 102, such as clamps, locks, posts, etc., and/or mechanisms to actuate features of the catheter 102, such as one or more actuator. In some embodiments, different versions of the modular plate 105 may be provided to support different configurations of the catheter 102, while maintaining a universal interface to the catheter positioning system 100. Thus, different modular plates 105 supporting different configurations of the catheter 102 may be swapped in and out for different procedures or applications. The sled 106 may be moved with a motor back and forth along the linear rail 104 and track 110, and the movement of the sled 106 may move the hoop drive assembly 108, the turret 103, the modular plate 105, and the catheter 102 along the linear rail 104 and track 110. In this manner, the catheter 102 may be advanced and retracted along the track 110 through the nose cone 116 and into or out of a patient. In an embodiment, the hoop drive assembly 108 may rotate the turret 103 in turn rotating the modular plate 105 and the catheter 102 held in the modular plate 105. In this manner, the catheter 102 may be rotated as needed to position the catheter 102 within the patient. In an embodiment, the modular plate 105 may include one or more actuators configured to move one or more control actuator of the catheter 102. The movement of the catheter 102 along the track, the rotation of the catheter 102, and/or the actuation of the one or more controls of the catheter 102 may enable an operator of the catheter positioning system 100 to position and/or use the catheter 102 in any way necessary for a desired operation.

Figure 2:
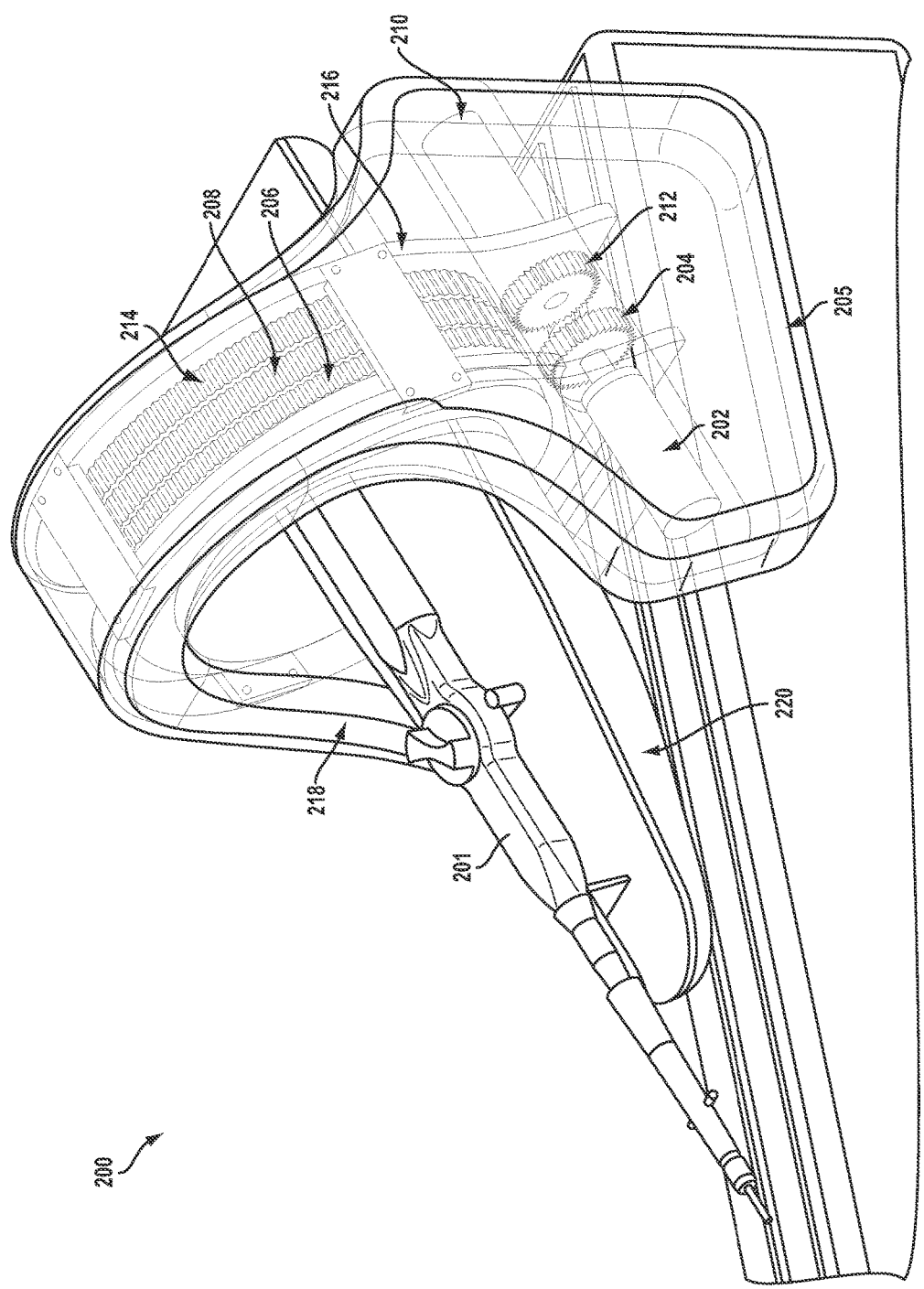
FIG. 2 is a cutaway perspective view of a hoop drive assembly according to an embodiment.

FIG. 2 illustrates components of an embodiment hoop drive assembly 200. In FIG. 2 the drive assembly enclosure 218, encasing the components of the hoop drive assembly 200 and a portion of the sled 205 on which the hoop drive assembly 200 is mounted, is illustrated as being transparent to enable internal components of the hoop drive assembly 200 to be seen. The hoop drive assembly 200 may include a first toothed ring 206 forming a first internal opening, a second toothed ring 208 forming a second internal opening, and a third toothed ring 214 forming a third internal opening. The first toothed ring 206, second toothed ring 208, and third toothed ring 214 may be aligned to rotate around a common axis of rotation. The internal openings of the first toothed ring 206, the second toothed ring 208, and the third toothed ring 214 may be aligned to form a common central opening within the hoop drive assembly. The common central opening may be configured to enable a portion of a turret 220 and/or a catheter 201 to pass within first internal opening of the first toothed ring 206, the second internal opening of the second toothed ring 208, and/or the internal opening of the third toothed ring 214. The first toothed ring 206, the second toothed ring 208, and the third toothed ring 214 may be supported by a frame 216 of the hoop drive assembly 200.

The first toothed ring 206, the second toothed ring 208, and the third toothed ring 214 may be aligned with each other such that the first toothed ring 206, the second toothed ring 208, and/or the third toothed ring 214 may rotate independently. In an embodiment, the first toothed ring 206, the second toothed ring 208, and the third toothed ring 214 may be directly adjacent to each other with bearings or other friction reducing items between them. In another embodiment, the first toothed ring 206, the second toothed ring 208, and the third toothed ring 214 may be spaced apart from each other with other elements (e.g., non-rotating rings, etc.) between them. In an embodiment, a frame 216 may be configured to hold the first toothed ring 206, the second toothed ring 208, and/or the third toothed ring 214 in place such that the first toothed ring 206, the second toothed ring 208, and/or the third toothed ring 214 may rotate independently and about a common axis of rotation.

In an embodiment, each toothed ring 206, 208, and 214 may be coupled to its own respective motor, and each motor may be configured in position, orientation and with a drive train to cause the rotation of its respective toothed ring 206, 208, and 214, such as in either direction about the common axis. As an example, the first toothed ring 206 may be coupled to a first motor 202 and the third toothed ring 214 may be coupled to a third motor 210. A motor for the second toothed ring 208 is not shown for ease of illustration of the other motors. The motors coupled to the toothed rings 206, 208, and 214 may be any type of motor, including servomotors. The servomotors may include a sensor providing position feedback to a servomotor controller. The motors may further be hydraulic motors (e.g., turbines), such as hydraulic motors suitable for use within magnetic resonance imaging (MRI) machines. The coupling of each toothed ring 206, 208, and 214 with its own respective motor may enable each motor to be controlled to independently rotate its respective toothed ring 206, 208, and 214. In an embodiment, the first motor 202 may be coupled to the first toothed ring 206 by a set of one or more drive gears 204, and the third motor 210 may be coupled to the third toothed ring 214 by another set of one or more drive gears 212. As an example, the set of one or more drive gears 204 may be a single drive gear rotated by a shaft of the motor 202. The teeth of the one or more drive gears 204 may interface with teeth on an outer circumference of the first toothed ring 206. In this manner, activation or actuation of the first motor 202 and rotation of the shaft of the first motor 202 may rotate the one or more drive gears 204 and the first toothed ring 206. As another example, the set of one or more drive gears 212 may be a single drive gear rotated by a shaft of the motor 210. The teeth of the one or more drive gears 212 may interface with teeth on an outer circumference of the third toothed ring 214. In this manner, activation or actuation of the second motor 210 and rotation of the shaft of the second motor 210 may rotate the one or more drive gears 212 and the third toothed ring 214. In an embodiment, one of the toothed rings 206, 208, or 214 may include a turret support to which the turret 220 may be coupled. In this manner, rotation of the given one of the toothed rings 206, 208, or 214 that includes the turret support may change an orientation of the turret support relative to the common axis of rotation of the first toothed ring 206, the second toothed ring 208, and the third toothed ring 214, thereby rotating the turret 220 coupled to the turret support, as well as a catheter 201, which may be positioned or placed on the turret 220.

Figure 3A:
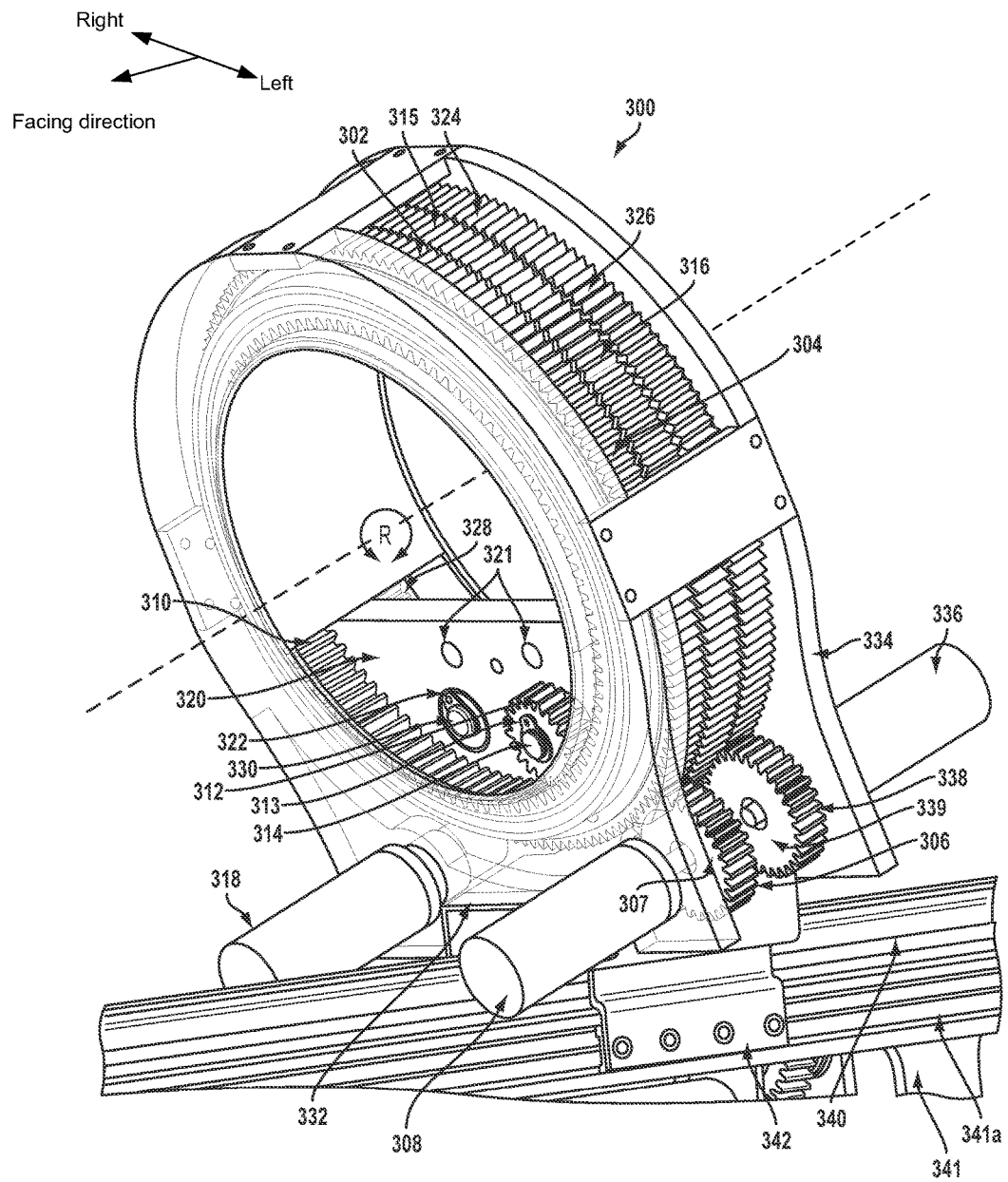
FIG. 3A-FIG. 3C are cutaway perspective views of a hoop drive assembly according to one or more additional embodiments.
Figure 3B:
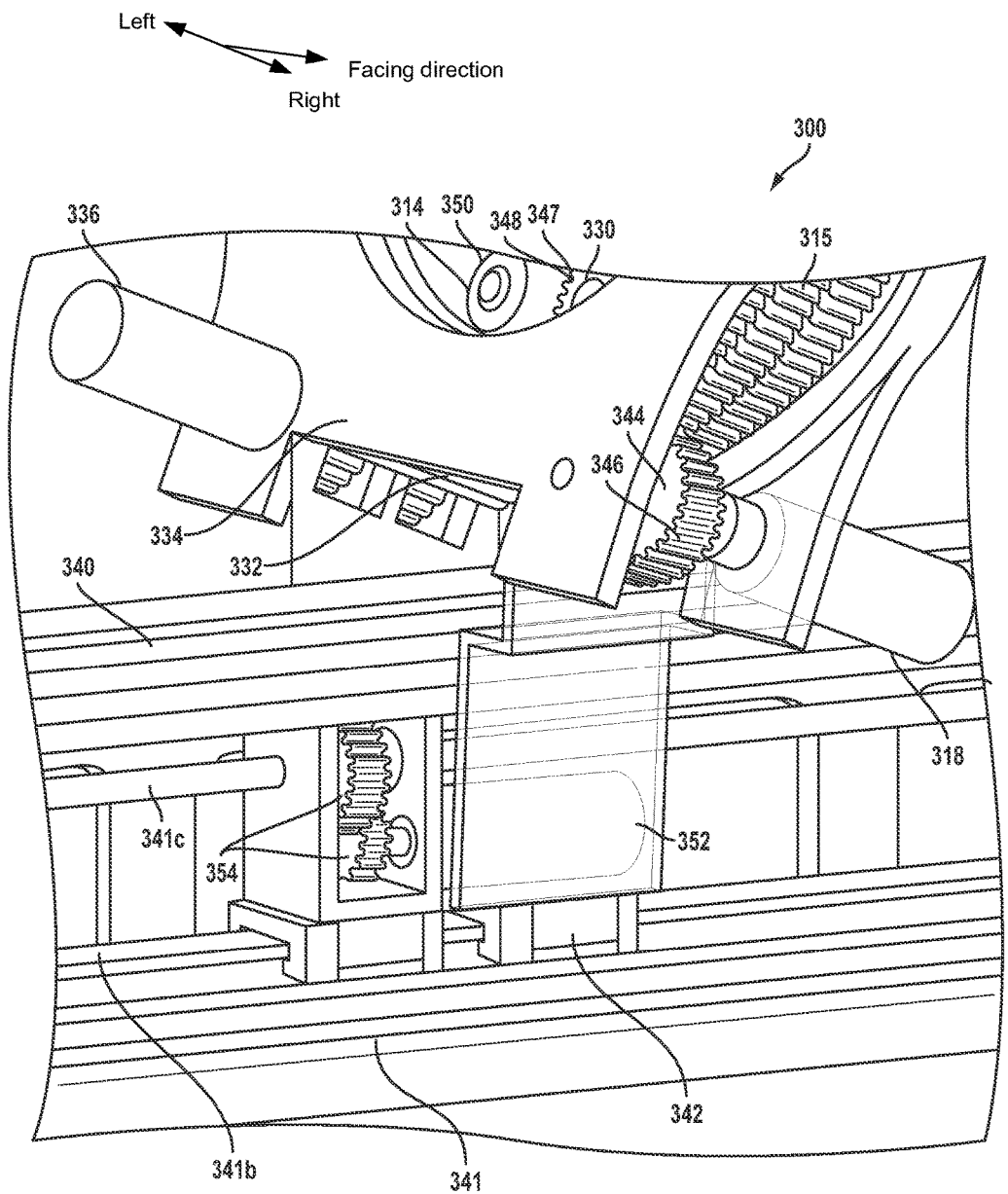
Figure 3C:
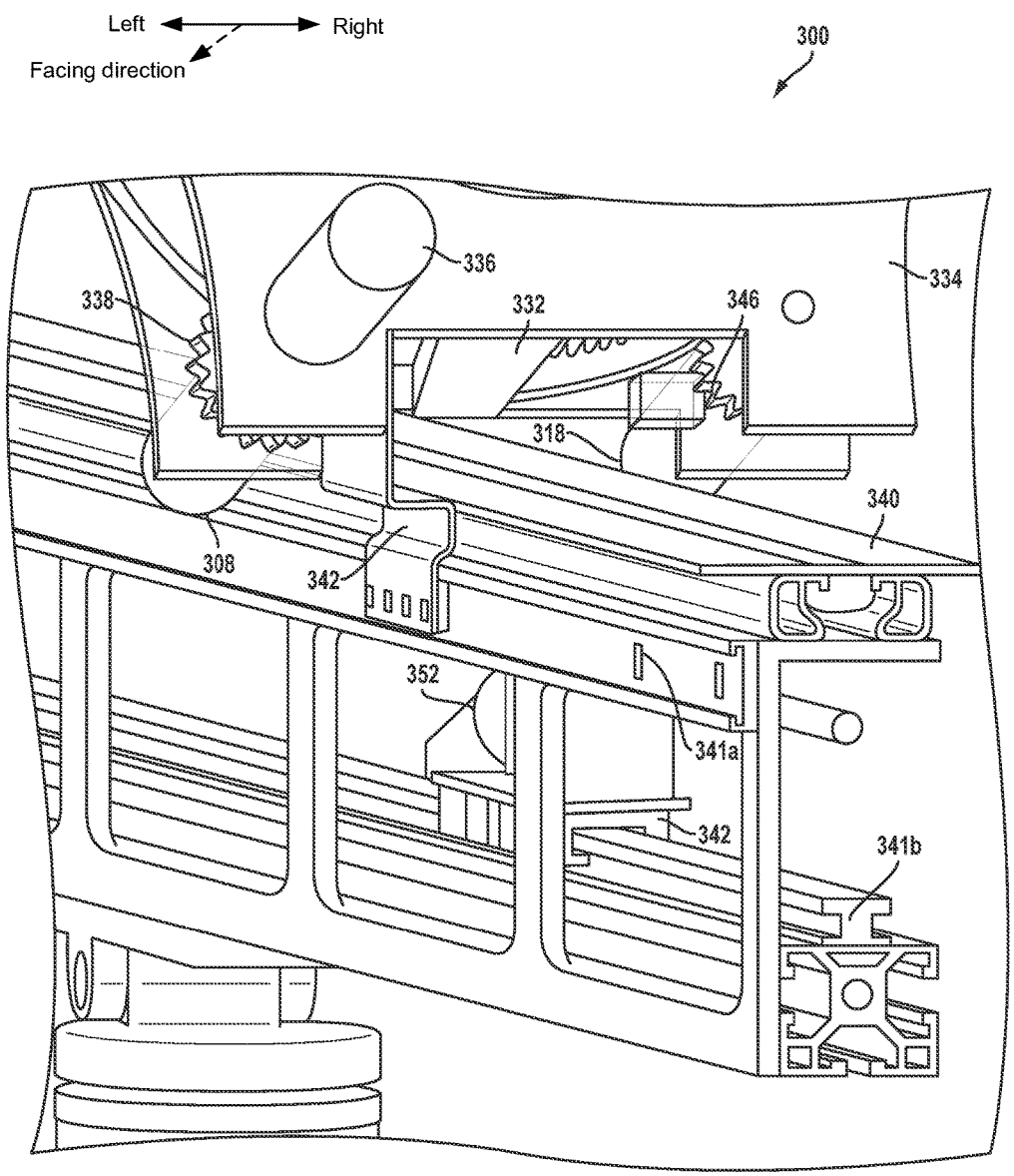

FIG. 3A through FIG. 3C illustrate components of an embodiment hoop drive assembly 300 of a catheter positioning system. The hoop drive assembly 300 is illustrated in FIG. 3A, FIG. 3B and FIG. 3C without a drive assembly enclosure, turret, modular plate, or catheter to better illustrate the internal components of the hoop drive catheter assembly 300. Additionally, the catheter positioning system is illustrated in FIG. 3A, FIG. 3B and FIG. 3C without other shielding to better show internal components of the linear rail 341 and sled 332. Referring to FIG. 3A, a front side, such as a front left side perspective view relative to an identified facing direction of the hoop drive assembly 300 is shown. The hoop drive assembly 300 may include a first toothed ring 302 having an outer circumference including a set of outer teeth 304 and an inner circumference including a set of inner teeth 310. The first toothed ring 302 may be configured to form a first internal opening surrounded by the set of inner teeth 310. The hoop drive assembly 300 may also include a second toothed ring 315 having an outer circumference including a set of outer teeth 316, an inner circumference, and a turret support 320. The turret support 320 may be an integral molded part of the second toothed ring 315 or may be a separate part attached to the inner circumference of the second toothed ring 315. The second toothed ring 315 may be configured to form an internal opening defined between the inner circumference of the second toothed ring 315 and the turret support 320. The hoop drive assembly 300 may include a third toothed ring 324 having an outer circumference including a set of outer teeth 326 and an inner circumference including a set of inner teeth 328. The first toothed ring 302, second toothed ring 315, and third toothed ring 324 may be aligned within a frame 334 of the hoop drive such that the first toothed ring 302, second toothed ring 315, and third toothed ring 324 may rotate independently around a common axis of rotation R.

The hoop drive assembly 300 may include three motors 308, 336, and 318. The motor 308 may be coupled to the outer teeth 304 of the first toothed ring 302, the motor 336 may be coupled to the outer teeth 326 of the third toothed ring 324, and the motor 318 may be coupled to the outer teeth 316 of the second toothed ring 315. The motors 308, 336, and 318 may be any type of motors, such as servomotors including a sensor providing position feedback to a servomotor controller. The motors 308, 336, and 318 may be connected to a system processor of the catheter positioning system including the hoop drive assembly 300, and the system processor may control the activation of one or more of the motors 308, 336, and 318 together and/or independently.

The motor 308 may be coupled to the outer teeth 304 of the first toothed ring 302 by a drive gear 307 attached to a shaft of the motor 308, and teeth 306 of the drive gear 307 may interface with the outer teeth 304 of the first toothed ring 302. In this manner, the motor 308 may rotate the drive gear 307 to rotate the first toothed ring 302 around the common axis of rotation R. The motor 336 may be coupled to the outer teeth 326 of the third toothed ring 324 by a drive gear 339 attached to a shaft of the motor 336, and teeth 338 of the drive gear 339 may interface with the outer teeth 326 of the third toothed ring 324. In this manner, the motor 336 may rotate the drive gear 339 to rotate the third toothed ring 324 around the common axis of rotation R. The motor 318 may be coupled to the outer teeth 316 of the second toothed ring 315 by a drive gear 344 (see FIG. 3B) attached to a shaft of the motor 318, and teeth 346 (see FIG. 3B) of the drive gear 344 (see FIG. 3B) may interface with the outer teeth 316 of the second toothed ring 315. In this manner, the motor 318 may rotate the drive gear 344 (see FIG. 3B) to rotate the second toothed ring 315 around the common axis of rotation R. Additionally, rotation of the second toothed ring 315 around the common axis of rotation R may change an orientation of the turret support 320 relative to the common axis of rotation R (e.g., may rotate the turret support 320 around the common axis of rotation R). By changing the orientation of the turret support 320 relative to the common axis of rotation R, rotation of the second toothed ring 315 may change the orientation of a turret coupled to the turret support 320 (e.g., may rotate the turret around the common axis of rotation R).

In an embodiment, the motors 308, 336, and 318 may be supported in the frame 334 of the hoop drive assembly 300. Location of the motors 308, 336, and/or 318 in the frame 334 of the hoop drive assembly 300 may enable the turret to rotate without having to break electrical and/or control connections for the motors 308, 336, and/or 318 across the path of rotation for the turret, for example using slip rings or other rotary connections. Additionally, locating the motors 308, 336, and/or 318 remote from the turret supporting the catheter may reduce the weight needed to be supported in the turret and may enable the motors 308, 336, and/or 318 to be moved to areas having improved shielding from fluid connections to the catheter and/or patient bodily fluids (e.g., blood).

The turret support 320 may include connection points 321 for coupling a turret to the turret support 320. The hoop drive assembly 300 may include a first gear drive 313 having a drive shaft 314 surrounded by a set of drive teeth 312. The first gear drive 313 may be rotationally coupled to turret support 320. For example, a portion of the drive shaft 314 may extend into an opening 350 (see FIG. 3B) in the turret support 320. In this manner the first gear drive 313 may be coupled to the turret support 320, but allowed to rotate. The drive shaft 314 may extend through the internal opening of the first toothed ring 302. The drive teeth 312 of the first gear drive 313 may interlock with the inner teeth 310 of the first toothed ring 302 such that rotation of the first toothed ring 302 rotates the first gear drive 313 and drive shaft 314. The hoop drive assembly 300 may include a second gear drive 348 (see FIG. 3B) having a drive shaft 330 surrounded by a set of drive teeth 347 (see FIG. 3B). The second gear drive 348 (see FIG. 3B) may be rotationally coupled to turret support 320. For example, a portion of the drive shaft 330 may extend through an opening 322 in the turret support 320 and into the internal opening in the first toothed ring 302. In this manner the second gear drive 348 (see FIG. 3B) may be coupled to the turret support 320, but allowed to rotate. The drive shaft 330 may also extend through the internal opening of the first toothed ring 302. The drive teeth 347 (see FIG. 3B) of the second gear drive 348 (see FIG. 3B) may interlock with the inner teeth 328 of the third toothed ring 324 such that rotation of the third toothed ring 324 rotates the second gear drive 348 (see FIG. 3B) and drive shaft 330.

In an embodiment, rotation of the second toothed ring 315 causing rotation of the turret support 320 about the common axis of rotation R may cause rotation of the first gear drive 313 and/or the second gear drive 348 because the first gear drive 313 and/or the second gear drive 348 may be rotationally coupled to the turret support 320. The system processor of the catheter positioning system including the hoop drive assembly 300 may compensate for such rotation of the first gear drive 313 and/or the second gear drive 348 by activating the first motor 308 to rotate the first toothed ring 302 and/or the second motor 336 to rotate the third toothed ring 324. In this manner, the system processor of the catheter positioning system including the hoop drive assembly 300 may control the activation of the first motor 308 and/or the third motor 336 to rotate the first toothed ring 302 and/or third toothed ring 302, respectively, to prevent the first gear drive 313 and/or the second gear drive 348 from rotating when the second toothed ring 315 causes rotation of the turret support 320.

The frame 334 of the hoop drive assembly 300 may be coupled to the sled 332. The sled 332 may support the hoop drive catheter assembly 300 above a track 340 of the linear rail 341. The sled 332 may be supported on the linear rail 341 by a side slide support 342 sliding along a side rail 341a of the linear rail 341 and a bottom slide support 342 (see FIG. 3B) sliding along a bottom rail 341b (see FIG. 3B) of the linear rail 341. Referring to FIG. 3B (which provides a rear right side perspective view of the hoop drive assembly 300), the sled 332 may include a sled motor 352 that may move the sled 332 along the linear rail 341 when actuated. As an example, the sled motor 352 may be coupled to a shaft 341c of the linear rail 341 by a set of drive gears 354. Actuation of the sled motor 352 may turn the set of drive gears 354 that may move the sled 332 and attached hoop drive assembly 300 along (e.g., forward and backward) the linear rail 341. In one example embodiment, the shaft 341c may be a threaded shaft or worm gear, which is threaded into a threaded opening of one of the gears in the set of drive gears 354. As the drive gear 354 is turned, the interaction of the inner threads of one of the set of drive gears 354 and the threads or worm gear of the shaft 241c may cause the sled 332 to move back and forth along a linear axis, such as along the linear rail 341, depending on the direction of rotation of the drive gears 354. In an embodiment, the sled motor 352 may be any type motor, such as a servomotor including a sensor providing position feedback to a servomotor controller. Referring to FIG. 3C, which illustrates a rear left side perspective view of the hoop drive assembly 300, the coupling of the sled 332 to the hoop drive assembly 300 and the support of the hoop drive assembly 300 above the track 340 of the linear rail 341 is shown.

Figure 4:
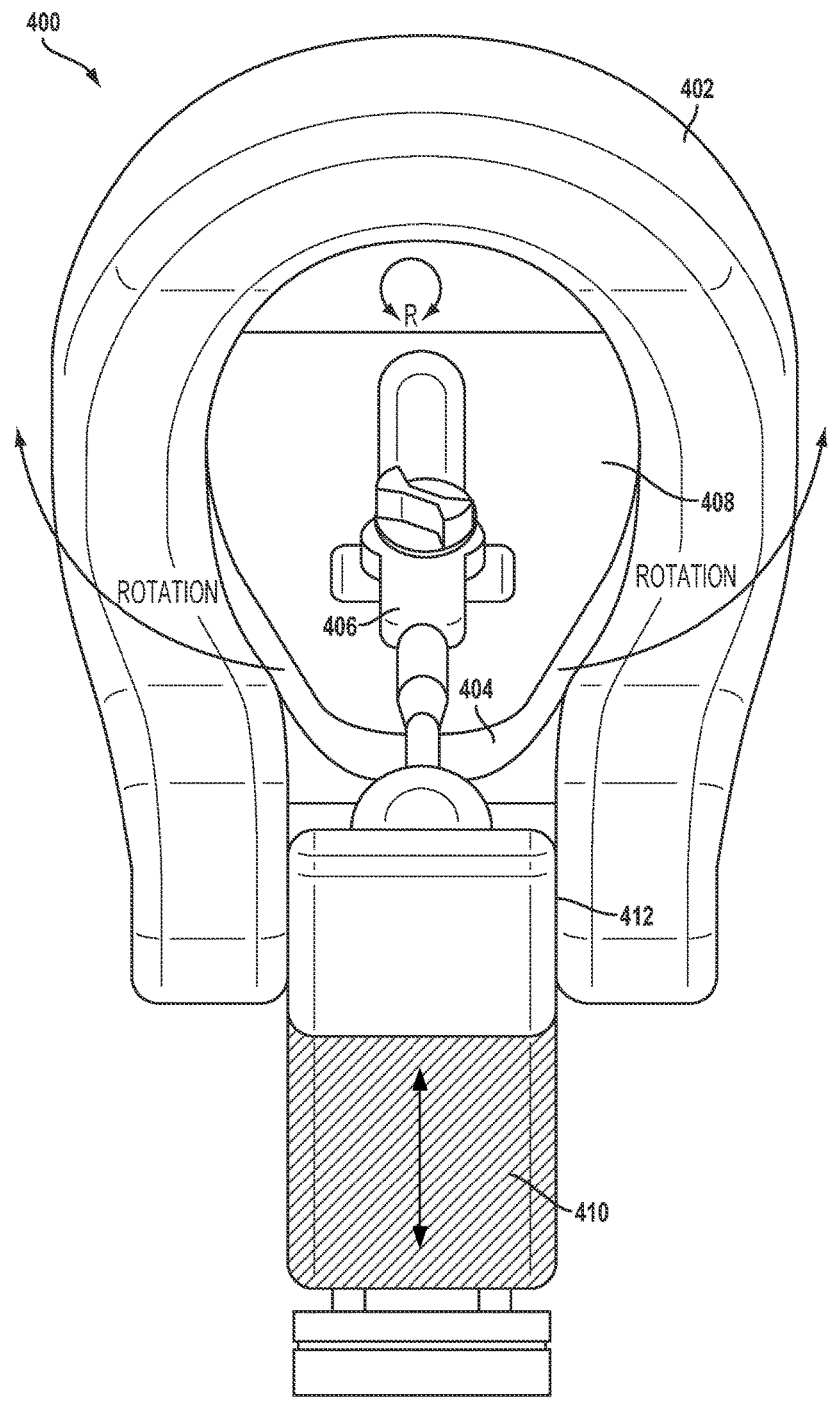
FIG. 4 is axial view of a hoop drive assembly according to a third embodiment.

FIG. 4 provides front view of a hoop drive assembly 400 according to an embodiment. As described above, the hoop drive assembly 400 may be mounted on a sled 412 that may move along a linear rail 410. The hoop drive assembly 400 and sled 412 may be encased by a drive assembly enclosure 402 that may shield the internal components of the hoop drive assembly 400 and sled 412 from fluid (e.g., blood, water, etc.) and other contaminants. The hoop drive assembly 400 may include a turret 404 and a modular plate 408 holding a catheter 406. The modular plate 408 may be removeably connected to the turret 404, such that one modular plate 408 may be replaced with another modular plate 408. In some embodiments, different versions of the modular plate 408 may be used to support different configurations of a catheter 406, while maintaining compatibility with the turret 404, such as through a catheter specific connection to the catheter 406 and a universal connection to the turret 404. In an embodiment, the turret 404 may be supported in the hoop drive assembly 400 such that turret 404, the modular plate 408 connected to the turret 404, and a catheter 406 held by the modular plate 408 may rotate in different rotational directions, such as a clockwise and counterclockwise direction of rotation around the common central axis of rotation R of the toothed rings of the hoop drive assembly 400. In an embodiment, the hoop drive assembly 400 may rotate through a full range of rotation 360 degrees or more in different directions, such as in a clockwise and in a counterclockwise direction of rotation around the common central axis of rotation R of the toothed rings of the hoop drive assembly 400.

Figure 5:
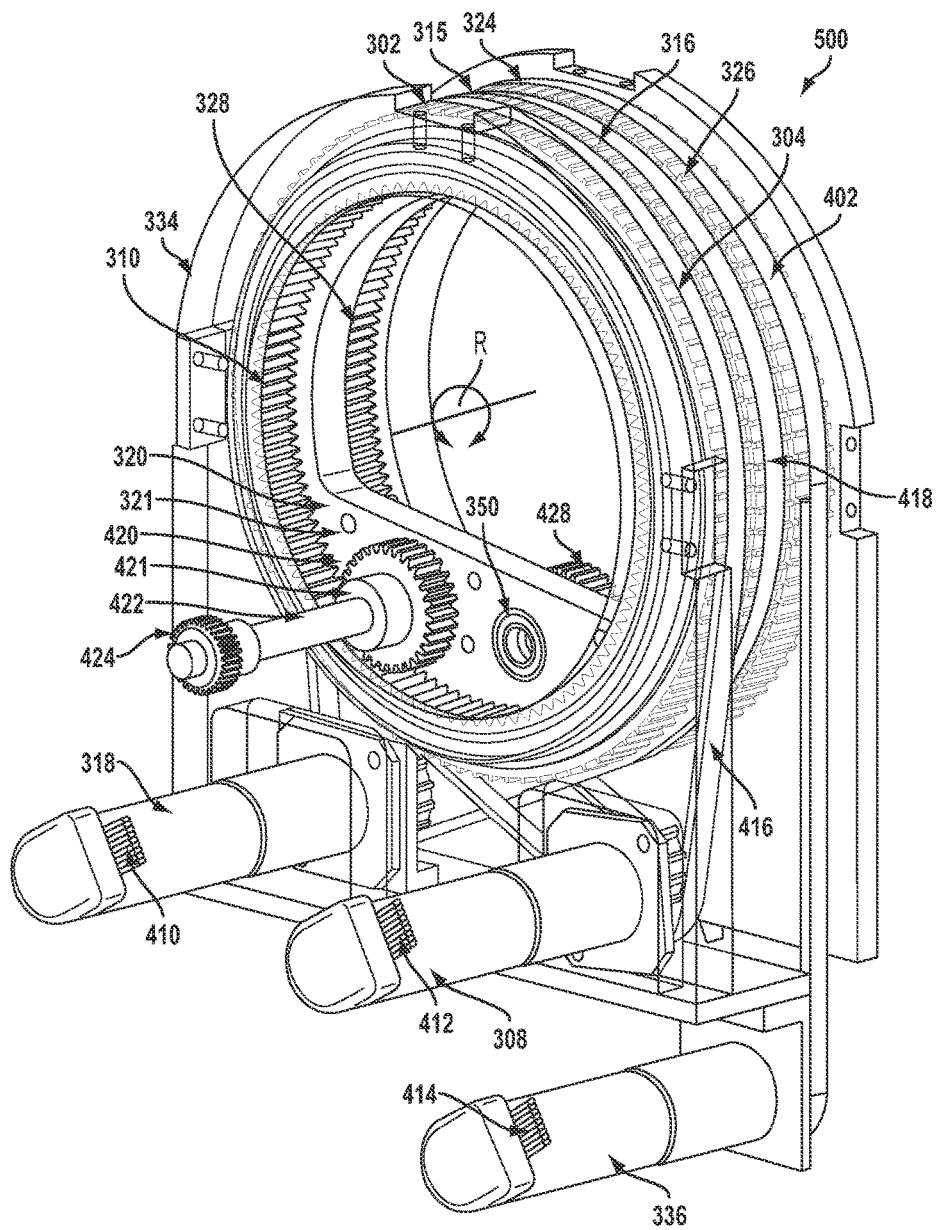
FIG. 5 is a cutaway perspective view of a hoop drive assembly according to a fifth embodiment.

FIG. 5 illustrates components of an embodiment hoop drive assembly 500 similar to the hoop drive assembly 300 illustrated in FIGS. 3A-3C, except that the motors 308, 318, and 336 of the hoop drive assembly 500 may be coupled to their respective toothed rings 302, 315, and 324 by drive belts 416, 418, and 402. Additionally, rather than extending out from different sides of the frame 334, the motors 308, 336, and 318 may extend out toward the same side of the frame 334. Such a placement of the motors 308, 336 and 318 may contribute to improved space efficiency. A first drive belt 416 may encircle the first toothed ring 302 and a shaft of a first motor 308. In this manner, rotation of the shaft of the first motor 308 may rotate the first drive belt 416, which in turn may rotate the first toothed ring 302. A second drive belt 418 may encircle the second toothed ring 315 and a shaft of a second motor 318. In this manner, rotation of the shaft of the second motor 318 may rotate the second drive belt 418, which in turn may rotate the second toothed ring 315. A third drive belt 418 may encircle the third toothed ring 324 and a shaft of a third motor 336. In this manner, rotation of the shaft of the third motor 336 may rotate the third drive belt 418 that may rotate the third toothed ring 324.

FIG. 5 also illustrates example wire connections or connectors 410, 412, and 414, which may be configured on the ends of to the first, second and third motors 318, 308, and 336, respectively. The wire connections or connectors 410, 412, and 414 may connect the motors 318, 308, and 336 to a system processor of the catheter positioning system, to power sources, etc. In an embodiment, the motors 318, 308, and 336 may send position data to the system processor and receive actuation signals from the system processor via the wire connections 410, 412, and 414.

Another difference between the hoop drive assembly 500 and the hoop drive assembly 300 illustrated in FIGS. 3A-3C is that gear drives 421 and 428 of the hoop drive assembly 500 are oriented on different sides on the turret support 320. A first gear drive 428 may have a drive shaft, which is not visible in the illustration. A second gear drive 421 includes drive teeth 420 surrounding the drive shaft 422. The drive shaft 422 may include a gear 424, such as a toothed gear, screw gear, etc. In an embodiment, the gear 424 may be configured/positioned to interface with an actuator driver of the turret supported by the turret support 320. In this manner rotation of the drive shaft 422 of the gear drive 421 may move the actuator driver of the turret supported by the turret support 320.

Figure 6:
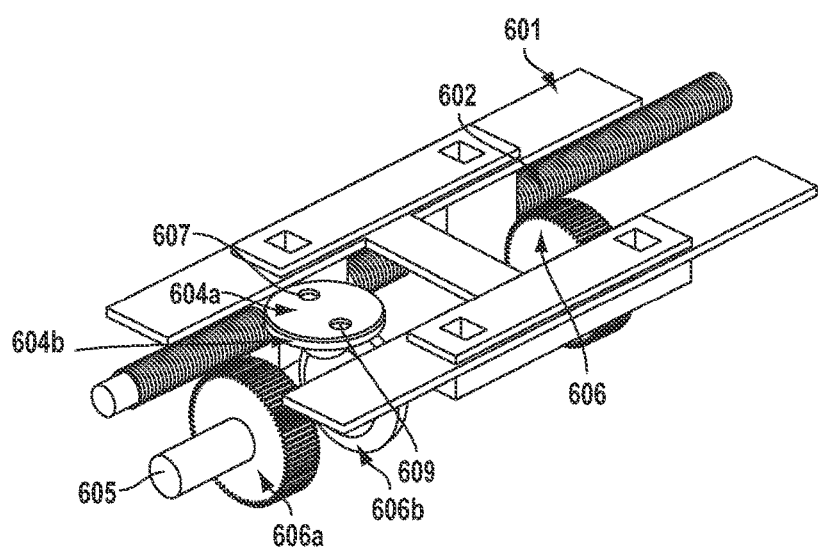
FIG. 6 is a perspective view of embodiment controlling actuators to move controls of a catheter.

FIG. 6 illustrates a first drive shaft 602 and a second drive shaft 605 of a first gear drive and second gear drive of a hoop drive assembly interfacing with a first actuator driver 604a and a second actuator driver 606a of the turret 601. In an embodiment, the first drive shaft 602 of the first gear drive may include a bevel gear 604b that may be configured to interface with the first actuator 604a, which may be a rotating linkage. The bevel gear 604b may further engage a bevel gear 606b, which may have an axis that is perpendicular to the axis of the bevel gear 604b, and which may have a beveled surface that may engage with a beveled surface of the bevel gear 604b. Rotation of the first drive shaft 602 caused by rotating one or more toothed rings of a hoop drive assembly may rotate the first actuator 604a of the turret 601. The first actuator 604a may include sockets 607, 609 for interfacing with other components, such as actuator parts of a modular plate that move a catheter control actuator. In the various embodiments, the first actuator driver 604a and the second actuator driver 606a of the turret 601 may be any type of actuators, such as interfaces providing linear action or rotating action, and the drive shafts 602 and 605 of the first gear drive and the second gear drive of the hoop drive assembly may be any type drive shafts, such as bevel gears, lead screws, toothed gears, flexible drives, etc.

Figure 7A:
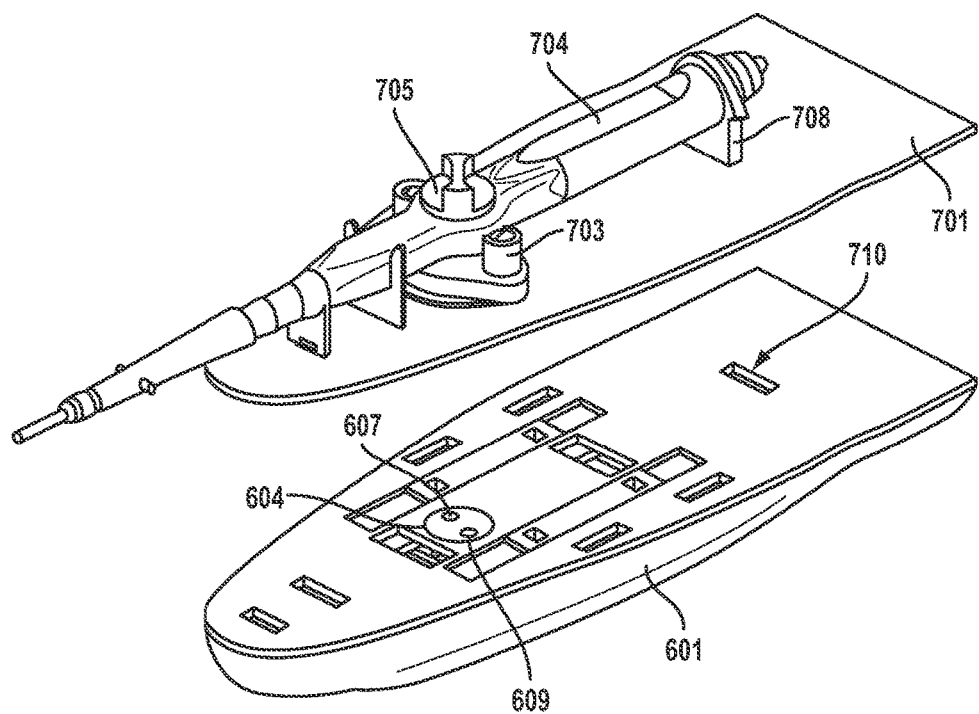
FIG. 7A is an oblique view of a catheter coupled with an example modular plate and components of the example sled member of FIG. 6.
Figure 7B:
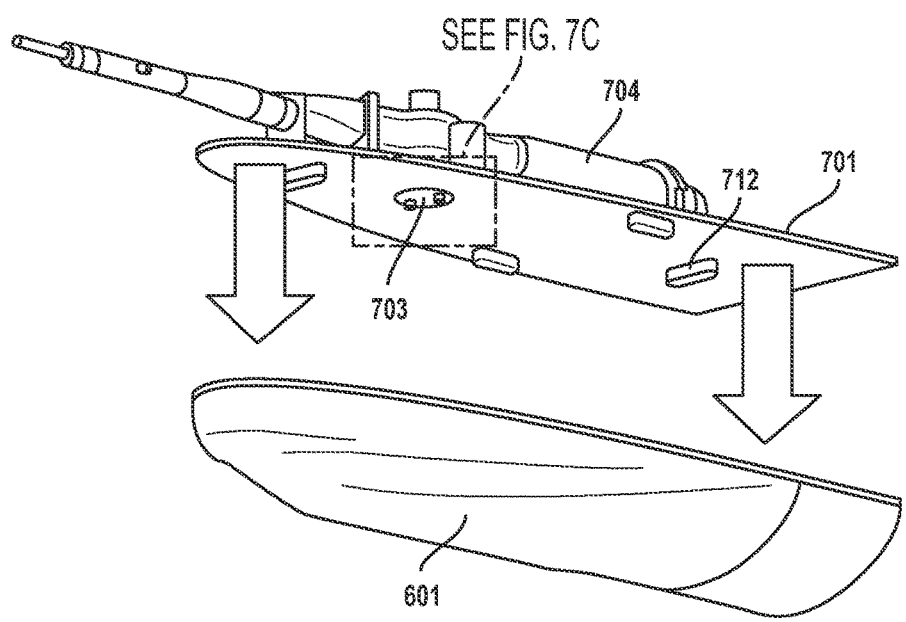
FIG. 7B is an exploded view of a catheter coupled with an example modular plate and components of the example sled member.
Figure 7C:
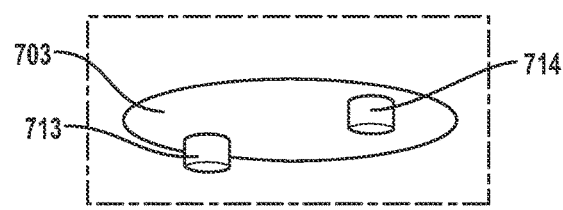
FIG. 7C is a diagram illustrating an embodiment actuator interface.

FIG. 7A, FIG. 7B and FIG. 7C illustrate aspects of the components of the turret 601 described above with reference to FIG. 6, along with an interfacing modular plate 701 holding a catheter 704. The catheter 704 may be coupled to the modular plate 701 and held in place by one or more clamps 708. The illustrated catheter 704 has a rotatable control actuator 705 that fits into an actuator interface 703 (e.g., a molded nest) that is part of the modular plate 701. In an embodiment, sensors on the modular plate 701 (e.g., such as circuits completed or opened by placing the catheter in the actuator interface 703 and/or closing or opening the clamps 708) may detect when the catheter 704 is positioned properly and/or improperly on the modular plate 701 and/or a type of catheter 704 held by the modular plate 701. In an embodiment, the turret 601 may include connection points 710 (e.g., slots configured to receive tabs 712 (illustrated in FIG. 7B) of the modular plate 701) for receiving and holding the modular plate 701 to the turret 601. In an embodiment, sensors on the turret 601 (e.g., such as circuits completed or opened by placing the tabs 712 into the connection points 710) may detect when the modular plate 601 is positioned properly and/or improperly on the turret 601 and/or the type of modular plate 701 and/or the type of catheter 704 held by the modular plate 701. In an embodiment, electrical contacts on the tabs 712 of the modular plate 601 may contact electrical contacts on the connection points 710 of the turret 601 when the modular plate 701 is coupled to the turret 710, thereby establishing an electrical connection between the modular plate 701 and turret 601. As illustrated in FIG. 7B, the actuator 703 of the modular plate 701 may include projections 713 and 714 configured to interface with sockets 607 and 609 of the first actuator 604 of the turret 601. In this manner, when the catheter is connected into the modular plate 701 that is connected to the turret 601, rotation of the drive shaft 602 caused by rotating one or more toothed rings of a hoop drive assembly may rotate the first actuator 604 of the turret 601, which in turn may move the actuator 703 of the modular plate 701 that may move the control actuator 705 of the catheter 704.

Figure 9:
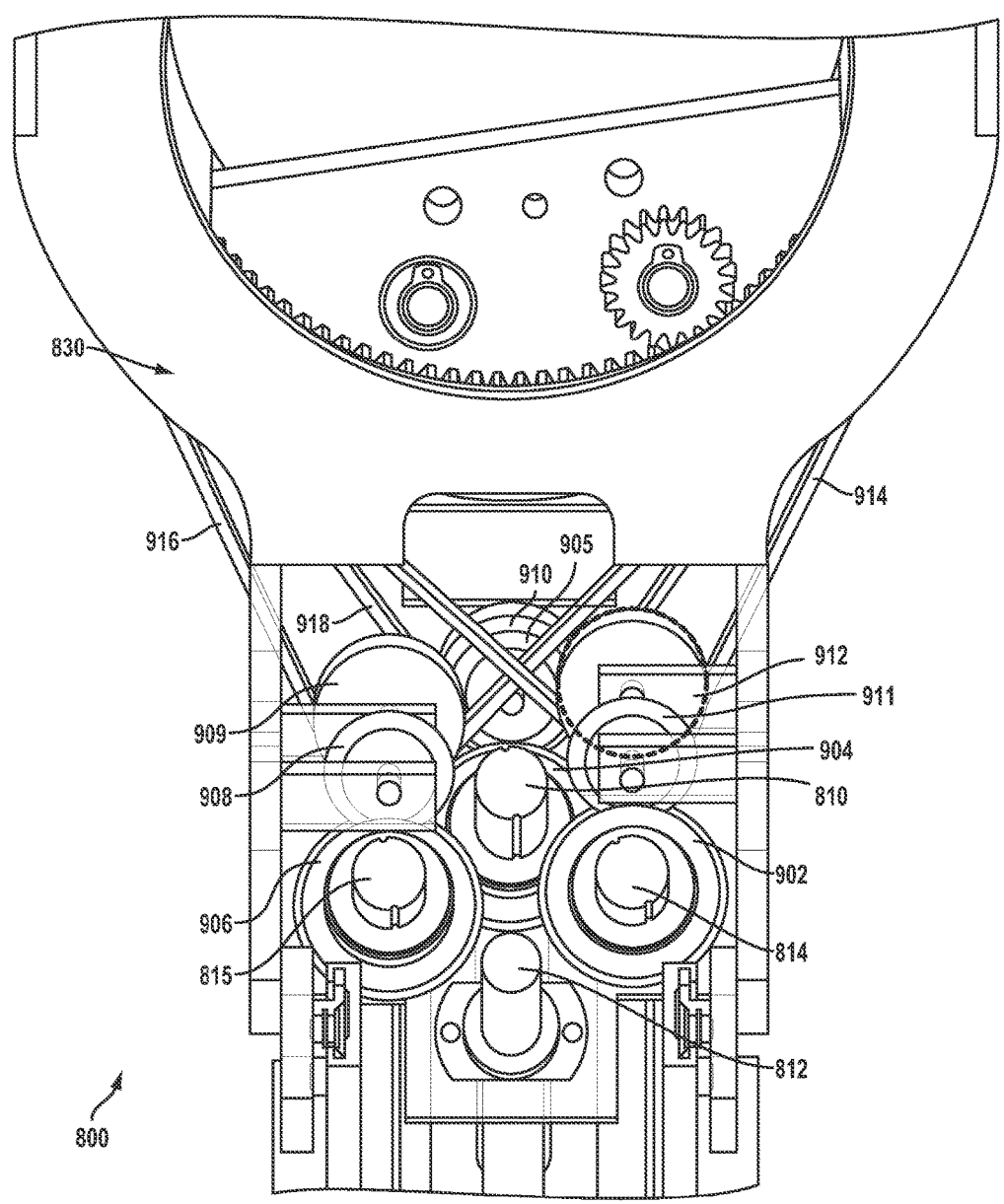

FIG. 8 and FIG. 9 illustrate components of a catheter positioning system 800 including a linear rail 820, a sled 816 configured to move along the linear rail 820, and a hoop drive assembly 801. Referring to FIG. 8, the hoop drive assembly 801 may include a first toothed ring 824, second toothed ring 826, and third toothed ring 828 supported in a frame 824 enclosed and supported within a structure, such as a hoop support frame 830. The hoop drive assembly 801 may also include a turret 822.

In catheter positioning system 800, the sled motor 806, the motor 808 coupled to the first toothed ring 824, the motor 802 coupled to the second toothed ring 826, and the motor 804 coupled to the third toothed ring 828 may be located remotely from the hoop drive assembly 801 and the sled 816. Motors 802, 804, 806, and/or 808 may be any type motor, such as a servomotor including a sensor providing position feedback to a servomotor controller. The sled motor 806 may be coupled to a drive shaft 812 (e.g., a screw gear) that, when rotated by the sled motor 806, may move the sled 816 and hoop drive assembly 801 along the linear rail 820. In an embodiment, the motor 808 may be coupled to the first toothed ring 824 via a motor drive shaft 814, the motor 802 may be coupled to the second toothed ring 826 via a motor drive shaft 815 (see also, FIG. 9), and the motor 804 may be coupled to the third toothed ring 828 via a drive shaft 810. In an embodiment, the motor drive shafts 810, 814, and/or 815 may be flexible drive shafts. While illustrated as being attached to the linear rail 820 in FIG. 8, the motors 802, 804, 806, and/or 808 need not be attached to the linear rail 820. With longer motor drive shafts 810, 814, and/or 815, the motors 802, 804, 806, and/or 808 may be located away from the linear rail 820, such as in a separate area outside an operating room in which the linear rail 820, sled 816, and the hoop drive assembly 801 are located. Locating the motors 802, 804, 806, and/or 808 remote from the turret 822 supporting the catheter, the hoop drive assembly 801, and the sled 816 may enable the turret 822 to rotate without having to break electrical and/or control connections for the motors 802, 804, 806, and/or 808 across the path of rotation for the turret 822 (e.g., using slip rings or other rotary connections) may reduce the weight needed to be supported in the turret 822 and/or sled 816, may enable the motors 802, 804, 806, and/or 808 to be moved to areas having improved shielding from fluid connections to the catheter and/or patient bodily fluids (e.g., blood), and/or may enable the motors 802, 804, 806, and/or 808 to be moved to areas where electromagnetic fields that may be generated by the motors 802, 804, 806, and/or 808 may be of less risk of interfering with catheter operations (e.g., to a designated safe distance from an electrophysiology catheter and/or patient at which the interference from stray fields is reduced).

Referring to FIG. 9, in an embodiment, the motor drive shafts 814, 815, and 810 may each interface with its own respective drive gear 902, 906, and 904. Drive gear 902 may be rotated by motor drive shaft 814 and may interface with drive gear 912, such as thorough an interface gear 911. The interface gear 911 may translate rotation of the drive gear 902 about a first axis into rotation of the drive gear 912 about a different axis. In some embodiments, the interface gear 911 (and the drive gear 902) may be a bevel gear, an offset gear, or other similar gear (or combinations thereof) that can translate rotation about different axes. In some embodiments, the interface gear 911 may include a beveled surface including gears or a friction surface that engages a similar mating surface on the drive gear 902. In some embodiments the interface gear 911 or the mounting of the interface gear 911 may be at least partially flexible. The flexibility of the interface gear 911 may accommodate any flexing that may occur in the drive shaft 814. For example, when the axis of the drive shaft 814 shifts, the contact between the drive gear 902 and the interface gear 911 may be maintained and rotation may be uninterrupted. Rotation of the drive gear 912 may rotate a drive belt 914 to rotate the first toothed ring 824.

Drive gear 906 may be rotated by motor drive shaft 815 and may engage an interface gear 908, similar to the interface gear 911 described above. The interface gear 908 may translate rotation of the drive gear 906 about a first axis into rotation of a drive gear 909 about a different axis. In some embodiments, as with the interface gear 911 (and the drive gear 902), the interface gear 908 (and the drive gear 906) may be a bevel gear, an offset gear, or other similar gear (or combinations thereof) that can translate rotation about different axes. In some embodiments, the interface gear 908 may include a beveled surface including gears or a friction surface that engages a similar mating surface on the drive gear 906. In some embodiments the interface gear 908 or the mounting of the interface gear 908 may be at least partially flexible. The flexibility of the interface gear 908 may accommodate any flexing that may occur in the drive shaft 815. For example, when the axis of the drive shaft 815 shifts, the contact between the drive gear 906 and the interface gear 908 may be maintained and rotation may be uninterrupted. Rotation of the drive gear 909 may rotate a drive belt 916 to rotate the second toothed gear 826.

The drive gear 904 may be rotated by the motor drive shaft 810 and may engage an interface gear 905, similar to the interface gears 908 and 911 described herein above. The interface gear 905 may translate rotation of the drive gear 904 about a first axis into rotation of a drive gear 910 about a different axis. In some embodiments, as with the interface gears 908, and 911 (and the drive gears 906 and 902), the interface gear 905 (and the drive gear 910) may be a bevel gear, an offset gear, or other similar gear (or combinations thereof) that can translate rotation about different axes. In some embodiments, the interface gear 905 may include a beveled surface including gears or a friction surface that engages a similar mating surface on the drive gear 904. In some embodiments the interface gear 905 or the mounting of the interface gear 905 may be at least partially flexible. The flexibility of the interface gear 905 may accommodate any flexing that may occur in the drive shaft 810. For example, when the axis of the drive shaft 810 shifts, the contact between the drive gear 904 and the interface gear 905 may be maintained and rotation may be uninterrupted. Rotation of the drive gear 910 may rotate a drive belt 918 to rotate the third toothed gear 828.

Figure 10:
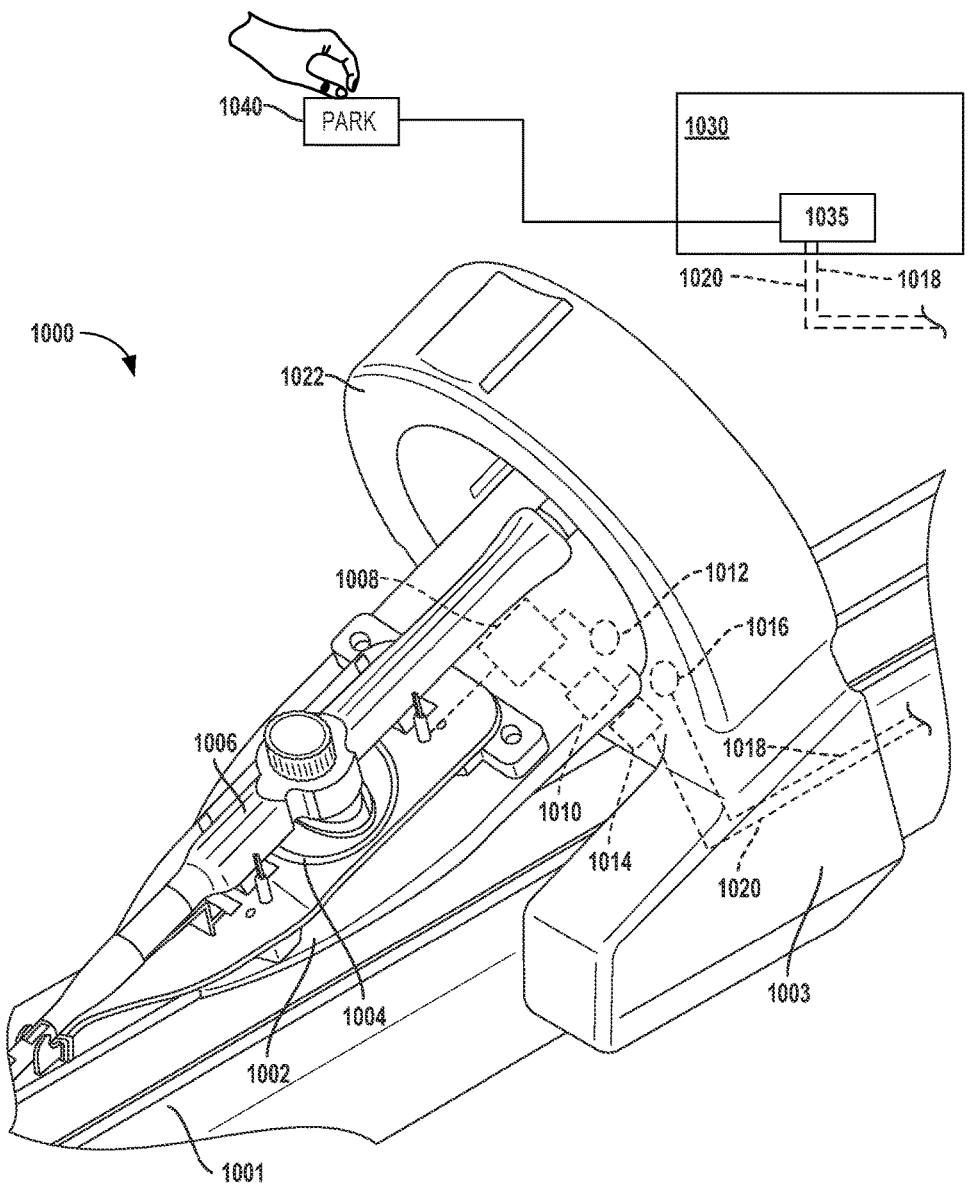
FIG. 10 is a perspective view of a catheter positioning system according to a third embodiment.

FIG. 10 illustrates a hoop drive assembly 1000 of a catheter positioning system including a linear rail 1001, a sled 1003, a turret 1002, and a modular plate 1004 holding a catheter 1006. A drive assembly enclosure 1022 may encase at least a portion of the hoop drive assembly 1000. The sled 1003 may include an inductive transmitter 1014 and an optical receiver 1016 each connected by a respective wired connection 1020 and 1018 to a system processor 1035 of a catheter positioning system 1030 including the catheter positioning device. As an example, the inductive transmitter 1014 may be an inductive coil configured to output power by generating an electric field in response to control signals from the system processor 1035. The optical receiver 1016 may be an optical receiver, such as an infrared (IR) datalink receiver configured to receive an IR signal and send an indication of the received IR signal to the system processor 1035. In an embodiment, the turret 1002 may include a processor 1008 connected to an inductive receiver 1010, an optical transmitter 1012, and the modular plate 1004. As an example, the inductive receiver 1010 may be an inductive coil configured to receive power from an electric field generated by the inductive transmitter 1014 to provide power for the processor 1008. The inductive receiver 1010 may selectively provide power to the processor 1008 under the control of the system processor 1035 such that the processor 1008 may remain in a low power or idle state until power is provided by the inductive transmitter 1014, or may be continuously powered as long as the inductive transmitter 1014 is energized under the control of the system processor 1035. When the inductive receiver 1010 provides power, the processor 1008 may determine a status associated with the modular plate 1004 and/or catheter 1006 held in the modular plate 1004, and/or other status information. The processor 1008 may output the determined status via the optical transmitter 1012 (e.g., an IR datalink transmitter) to the optical receiver 1016. The determined status may be communicated from the optical receiver 1016 to the system processor 1035 via the connection 1018.

In some embodiments, inductive power may be provided to the processor 1008 and optical communication between the processor 1008 and the system processor 1035 may be conducted under specific conditions. For example, motors driving the toothed rings of the hoop drive assembly may be activated to align the inductive receiver 1010 of the turret 1002 with the inductive transmitter 1014 of the sled 1003 and to align the optical transmitter 1012 with the optical receiver 1016 in response to a park position indication from the system processor 1035 of the catheter positioning system 1030. In an embodiment, the park position indication may be generated in response to a button press event indication on a remote controller 1040 of the catheter positioning system 1030. In an embodiment, power to the turret processor may only be provided from the sled when the turret is in the park position. In an embodiment, the park position may be entered upon initial startup of the catheter positioning system 1030 to enable the system processor 1035 to gather data about the catheter 1006, modular plate 1002, and/or turret 1010 from the turret processor 1008.

In an embodiment, the determined status about the catheter 1006, modular plate 1002, and/or turret 1010 from the turret processor 1008 may be one or more of a catheter type, an indication of a correct modular plate alignment, an indication of an incorrect modular plate alignment, an indication a correct catheter alignment, an indication an incorrect catheter alignment, an indication of a first toothed ring alignment, an indication of a second toothed ring alignment, and/or an indication of a third toothed ring alignment.

Figure 11:
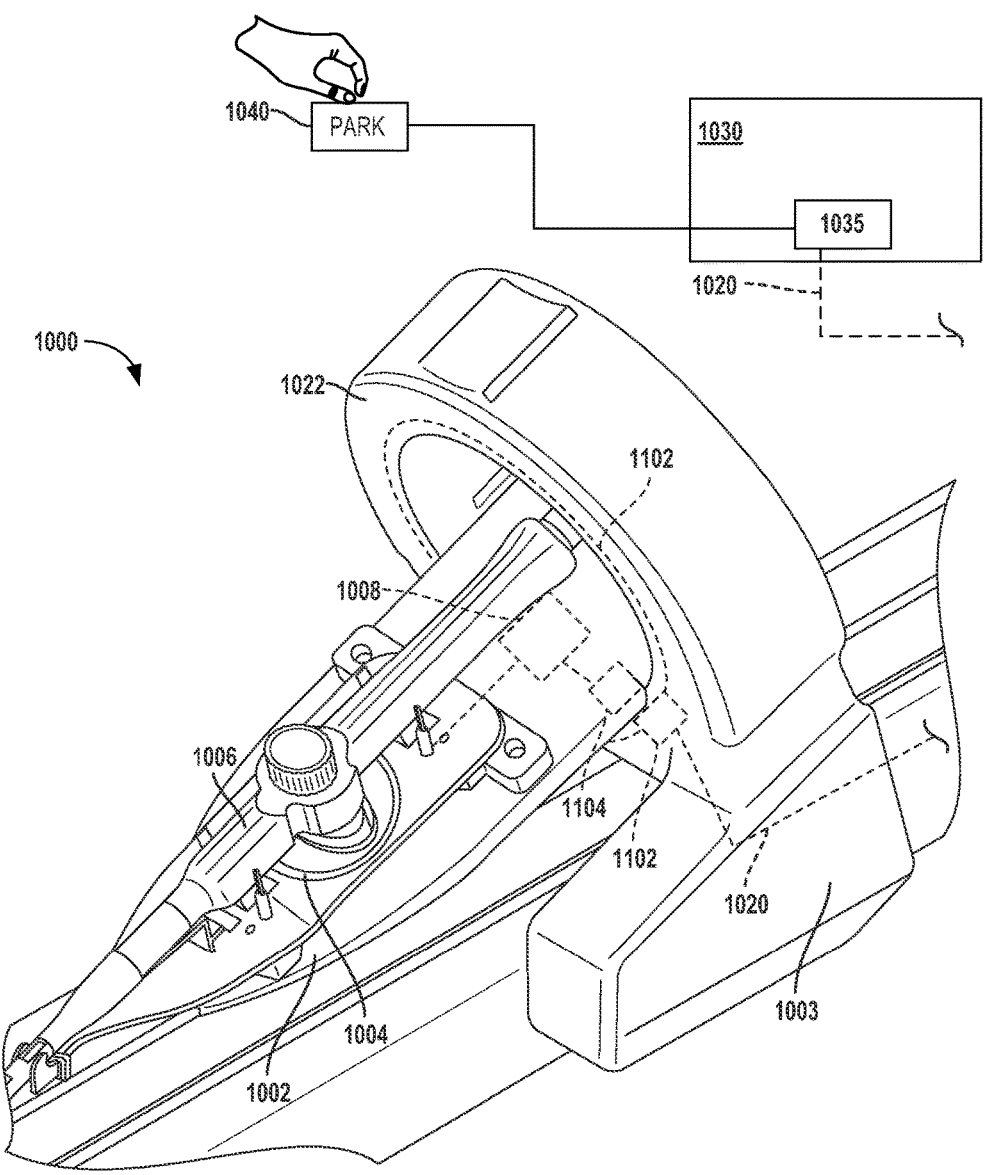
FIG. 11 is a perspective view of a catheter positioning system according to a fourth embodiment.

FIG. 11 illustrates an alternative embodiment for the hoop drive assembly 1000 of a catheter positioning system similar to the hoop drive assembly illustrated in FIG. 10. In such embodiments, an inductive transceiver 1102 in the sled 1003 may provide power to an inductive transceiver 1104 of the turret 1002 connected to the turret processor 1008 and may receive information signals from the inductive transceiver 1104 of the turret 1002. The inductive transceiver 1104 of the turret 1002 may generate signals indicating a status associated with the modular plate 1004 and/or catheter 1006 held in the modular plate 1004, and/or other status information determined by the turret processor 1008. The inductive transceiver 1102 of the sled 1003 may receive the signals and provide the signals, or a suitable indication of the signals, to the system processor 1035. In an embodiment, at least a portion of the inductive transceiver 1102 may be configured in a fixed position in the sled 1003. The inductive transceiver may include an inductive coil 1102 located in a portion of the drive assembly enclosure 1022 that may form an internal opening surrounding a portion of the turret 1002 that includes the inductive transceiver 1104. In this manner, inductive power from the inductive transceiver 1102 of the sled 1003 may be received continuously, or at any time by the inductive transceiver 1104 of the turret 1002, such as irrespective of the turret 1002 orientation within the drive assembly enclosure 1022. In other words, a parking position, as described herein in connection with FIG. 10, may not be necessary to power the processor 1008.

Figure 12:
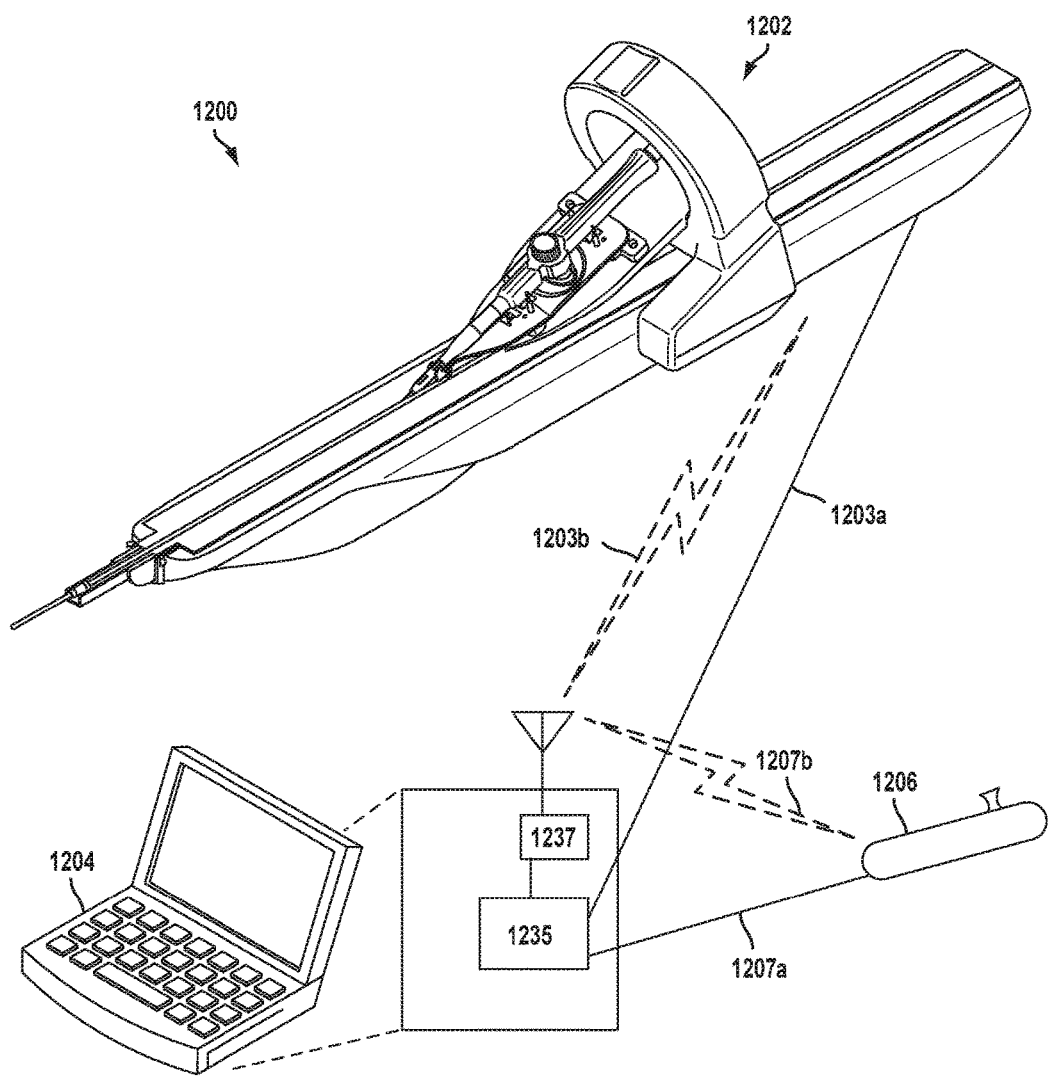
FIG. 12 is a system diagram illustrating components of an embodiment catheter positioning system.

FIG. 12 is a system block diagram illustrating components of an embodiment catheter positioning system 1200. A remote controller 1206 may be connected to a system processor 1235 of a programmable control system 1204 by one or more of a wired connection 1207a or a wireless data link 1207b, such as through a wireless connection to a radio module 1237 of the programmable control system 1204. The system processor 1235 of the programmable control system 1204 may also be connected to the catheter positioning system 1202 by one or more of a wired connection 1203a or a wireless data link 1203b, such as through a wireless connection to the radio module 1237.

The system processor 1235 of the programmable control system 1204 may output control signals to actuate the motors of the hoop drive assembly of the catheter positioning system 1200 based on inputs from the remote controller 1206 and/or on a calibration, training or programming sequence. For example, a calibration, training or programming sequence may include predetermined actions, such as programmed movements for automatic positioning of the catheter. Programmed movements of the catheter positioning system 1202 may be input prior to a medical procedure, such as by entering commands into the system processor of a programmable control system 1204 (e.g., via a keyboard) or by training the system, such as through manipulation of the remote controller 1206. In particular, the programmable control system 1204 may be configured with processor-executable instructions to issue drive or power commands to each of the motors in the hoop drive assembly to control the relative rotations of each motor so as to rotate the turret without rotating an actuator drive, rotate one actuator drive without rotating the turret, move both actuator drives without rotating the turret, and/or rotate the turret and one or more actuator drives simultaneously but independently. Further, the programmable control system 1204 may perform operations to control the speeds of the various motors in the hoop drive to control and/or prevent actuator mechanism interactions and/or cross talk. The programmable control system 1204 may implement various control and/or checking algorithms to control the operations of the various motors in the hoop drive. In an embodiment, the programmable control system 1204 may store different user profiles for different users of the remote controller 1206. The user profiles may include user selected levels for configurable settings of the catheter positioning system 1202, such as speed and resolution of the various motors, etc. of the catheter positioning system 1202. The programmable control system 1204 may identify the current user of the remote controller 1206, for example via a user log in, retrieve current the user's profile from a memory, and adjust the configurable settings to the selected levels indicated in the user profile. In this manner, configurable settings may be tailored to fit specific users of the remote controller 1206. Additionally, the programmable control system 1204 may record all movements, activations, positions, users, diagnostics, and any other data about the remote controller 1206 and/or catheter positioning system 1202 in one or more data files. The one or more data files may be system wide data files or may be specific files associated with a particular user or users. The one or more data files of information about the remote controller 1206 and/or catheter positioning system 1202 may be useful in service and/or maintenance of the catheter positioning system 1200 and/or may serve as data repositories for information associated with potential litigation related to use of the catheter positioning system 1200.

Figure 13:
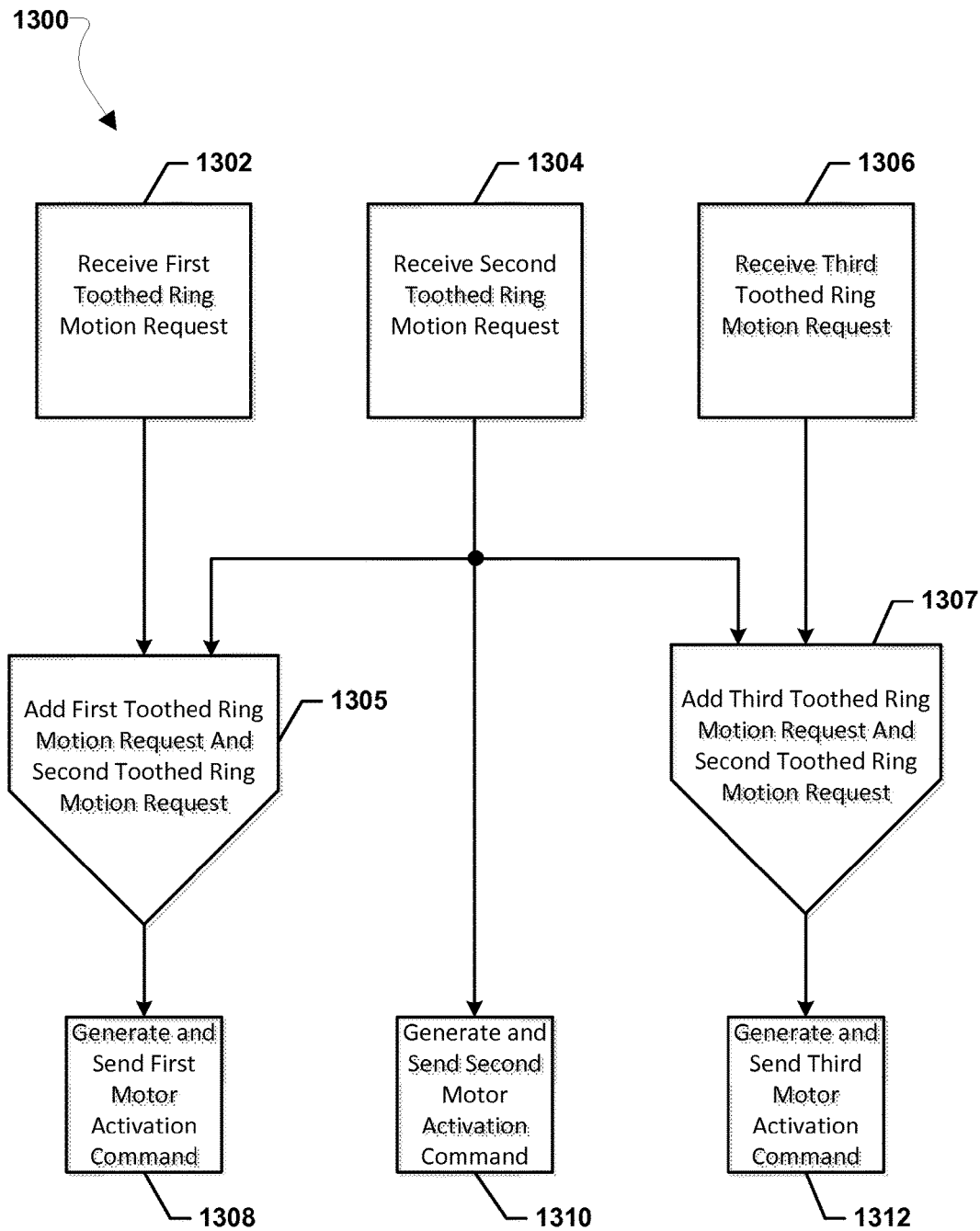
FIG. 13 is a process flow diagram illustrating an embodiment method for asynchronously generating hoop drive commands.

FIG. 13 illustrates an embodiment method 1300 for asynchronously generating hoop drive commands to control a three toothed ring hoop drive. In some embodiments, the operations of the embodiment method 1300 may be performed by a processor of a programmable control system connected to a first motor, a second motor, and a third motor of a three toothed ring hoop drive assembly. Activation of the first motor may drive a first toothed ring to rotate about an axis of rotation, activation of the second motor may drive a second toothed ring to rotate about an axis of rotation, and activation of the third motor may drive a third toothed ring to rotate about an axis of rotation. Rotation of the first toothed ring may control a first actuator drive, rotation of the second toothed ring may rotate a turret, and rotation of the third toothed ring may control a second actuator drive. The rotations of each motor may be controlled relative to one or more of the other motors so as to rotate the turret without rotating an actuator drive, rotate one actuator drive without rotating the turret, move both actuator drives without rotating the turret, and/or rotate the turret and one or more actuator drives simultaneously but independently. Rotations of the motors in the above described manner may provide a way for an operator, such as an operator of a remote controller, to achieve a variety of positions of a catheter with a degree of flexibility, control and precision.

In block 1302 the processor may receive a first toothed ring motion request, in block 1304 the processor may receive a second toothed ring motion request, and in block 1306 the processor may receive a third toothed ring motion request. In some embodiments, the motion requests in blocks 1302, 1304, and 1306 may be received for all toothed rings, if present. However, in some embodiments, motion requests for all rings may not be present. In such cases, the absence of a motion request for one or more of the toothed rings may be interpreted as a respective motion request for "zero" motion for the corresponding toothed rings. In other embodiments, the processor may receive requests only for those toothed rings that require movement. The first toothed ring motion request, second toothed ring motion request, and/or third toothed ring motion requests received by the processor in one or more of blocks 1302, 1304, and 1306 may be speed inputs such as analog voltage levels or digital signals indicative or a desired speed level, which may be received from a remote controller, and which may be generated by the remote controller in response to manipulation of controls (e.g., joysticks, buttons, wheels, knobs, etc.) on the remote controller. The first toothed ring motion request, second toothed ring motion request, and/or third toothed ring motion requests in blocks 1302, 1304, and 1306 may be generated and received independent of each other. The motion requests may further include commands for a desired speed level, rotational value, or other value which the processor may transform into a necessary voltage level or other parameter required to achieve the specified speed, rotational value, or other value.

In block 1305, the processor may add the first toothed ring motion request and second toothed ring motion request together. The processor may add the first and second motion requests so as to compensate for any potentially conflicting requests or cumulative requests. In block 1308 the processor may use the sum of the first toothed ring motion request and second toothed ring motion request to generate and send a first motor activation command (e.g., a voltage, stepper signal, encoder pulses, etc.) to the first motor. In this manner, the motor activation command for the first motor may drive the first toothed ring at a speed that accounts for both the requested rotation speed of the first toothed ring as well as any requested rotation speed of the second toothed ring. In block 1310 the processor may generate and send a second motor activation command (e.g., a voltage, stepper signal, encoder pulses, etc.) based on the second toothed ring motion request. In block 1307 the processor may add the third toothed ring motion request and second toothed ring motion request together and in block 1312 the processor may use the sum of the third toothed ring motion request and second toothed ring motion request to generate and send a third motor activation command (e.g., a voltage, stepper signal, encoder pulses, etc.) to the first motor. In this manner, the motor activation command for the third motor may drive the third toothed ring at a speed that accounts for both the requested rotation speed of the third toothed ring as well as any requested rotation speed of the second toothed ring. In an embodiment, the processor may perform the operations of blocks 1305, 1308, 1307, 1310, and 1312 continuously as first toothed ring motion requests, second toothed ring motion requests, and/or third toothed ring motion requests are received.

Figure 14:
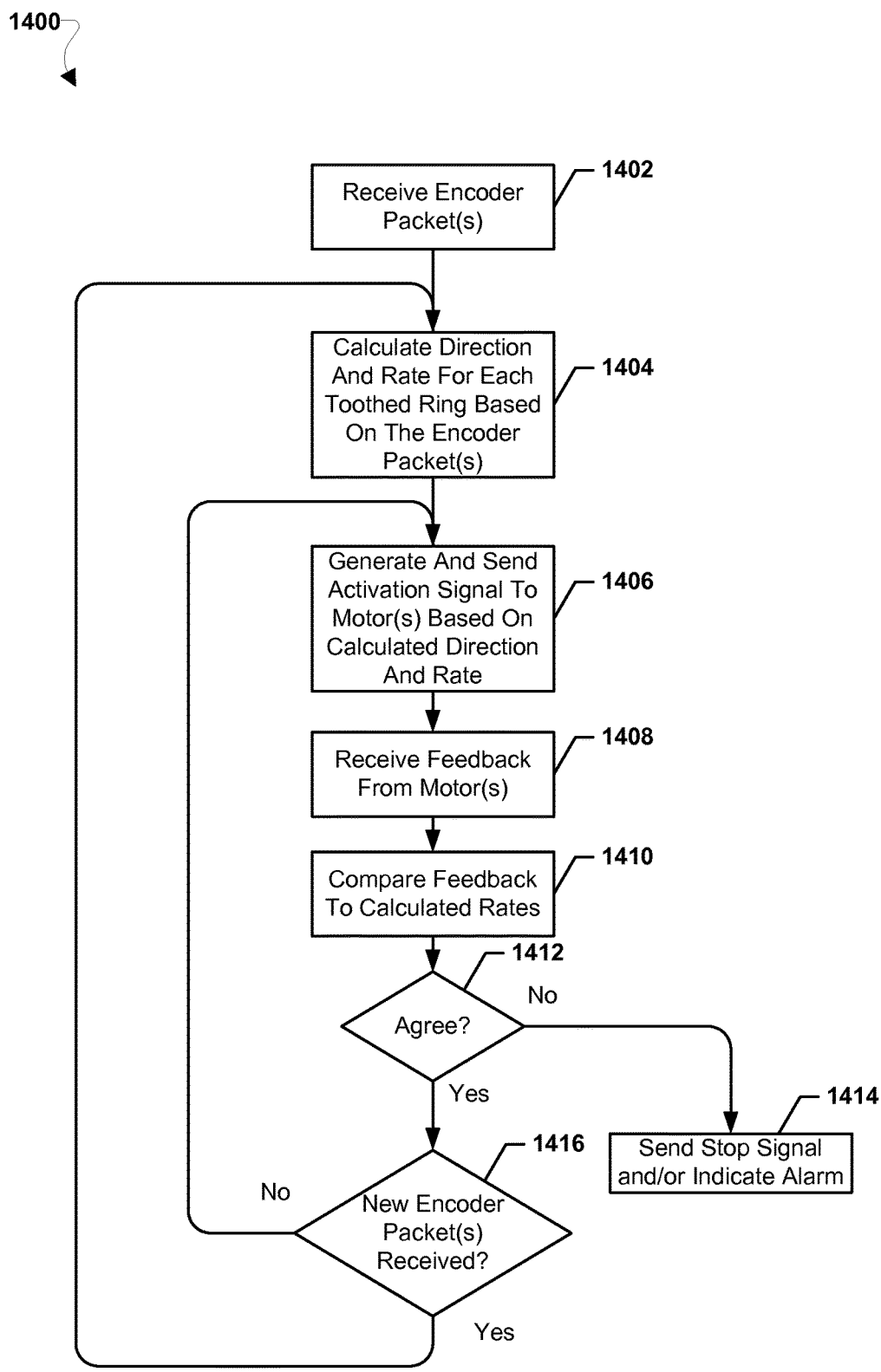
FIG. 14 is a process flow diagram illustrating an embodiment method for synchronous generation of hoop drive commands.

FIG. 14 is a process flow diagram illustrating an embodiment method 1400 for synchronous generation of hoop drive commands. In an embodiment, the operations of embodiment method 1400 may be performed by a processor of a programmable control system connected to a first motor, a second motor, and a third motor of a three toothed ring hoop drive assembly. Activation of the first motor may drive a first toothed ring to rotate, activation of the second motor may drive a second toothed ring to rotate, and activation of the third motor may drive a third toothed ring to rotate. Rotation of the first toothed ring may control a first actuator drive, rotation of the second toothed ring may rotate a turret, and rotation of the third toothed ring may control a second actuator drive. The rotations of each motor may be controlled relative to one or more of the other motors so as to rotate the turret without rotating an actuator drive, rotate one actuator drive without rotating the turret, move both actuator drives without rotating the turret, and/or rotate the turret and one or more actuator drives simultaneously but independently.

In block 1402 the processor may receive one or more encoder packets. The encoder packet(s) may be generated base on inputs from one or more encoders of a remote controller. Each encoder packet may indicate the first toothed ring, second toothed ring, or third toothed ring and a number of encoder pulses representing a requested motion of the respective indicated toothed ring of the hoop drive assembly. Alternatively, an encoder packet may be generated containing all of the requested motion information (e.g., including "zero" motion) for each toothed ring. In other embodiments, the processor may simply receive uncoordinated or asynchronous data packets or other asynchronous data (e.g., data that is not packetized), which reflects motion encoding for the toothed rings.

In block 1404 the processor may calculate a direction and a rate for each toothed ring based on the information from the encoder packet(s) received in block 1402. In an embodiment, the encoder pulse indication, or other information contained in an encoder packet may be a positive value of pulses or a negative value of pulses. A positive value may indicate a toothed ring is to be moved in a first direction, such as clockwise direction, while a negative value may indicate the toothed ring is to be moved in a second direction, such as a counter clockwise direction. The rotation rate of the second toothed ring controlling the rotation of the turret may be calculated as equal to the number of encoder pulses for the second toothed ring multiplied by the degree of rotation for each encoder pulse divided by an interval between packets. For example, when the degree of rotation for each encoder pulse for the second toothed ring is one degree and the interval between packets is one millisecond, a three encoder pulse indication in the encoder packet for the second toothed ring may result in a calculated three degree per millisecond rotation rate for the second toothed ring.

The rotation rate of the first and third toothed rings may be calculated as equal to the calculated rotation rate of the second toothed ring plus the number of encoder pulses for the first or third toothed ring, respectively, multiplied by the degree of rotation for each encoder pulse divided by an interval between packets. Continuing with the example discussed above in which three degrees per millisecond was the calculated rotation rate for the second toothed ring, when the degree of rotation for each encoder pulse for the first toothed ring is one degree, a two encoder pulse indication in the encoder packet for the first toothed ring may result in a calculated rotation rate of the first toothed ring of five degrees per millisecond. In an embodiment, the degree of rotation for each encoder pulse may be a fixed value. In another embodiment, the degree of rotation for each encoder pulse may be a variable value.

In block 1406 the processor may generate and send an activation signal to the first, second, and/or third motors based on the calculated direction and rate to activate one or more of the motors to rotate their respective toothed rings and rotate the turret and/or activate the actuators. In some embodiments, the processor may generate the activation signals corresponding to information from the encoding packets and send the activation signals to the motors as pulse signals. In block 1408 the processor may receive a feedback signal from the motor(s) and/or encoders associated with the motor(s). The feedback signals may be indications of the rate of rotation of the motors.

In block 1410 the processor may compare the feedback signals to the calculated rates or amounts of rotation, such as to determine that the activation signals had the intended effect on the rotation of the one or more motors. In determination block 1412 the processor may determine whether the calculated rate or amount of rotation and the actual rate or amount of rotation indicated by the feedback signals agree. In response to determining that the calculated and actual rates do not agree (i.e., determination block 1412="No"), in block 1414, the processor may send a stop signal to the motors and/or may indicate an alarm condition.

In response to determining that the calculated and actual rates agree (i.e., determination block 1412="Yes"), in determination block 1416 the processor may determine whether new encoder packet(s) have been received. In response to determining that new encoder packet(s) are not received (i.e., determination block 1416="No"), in block 1406 the processor may continue to generate and send activation signals to the motors based on the previously calculated direction and amount or rate. In the event that the encoder packets have specified an amount of movement, and the movement has been achieved based on the feedback, no further activation may be required. In response to determining that new encoder packet(s) are received (i.e., determination block 1416="Yes"), in block 1404 the processor may calculate the direction and rate for each toothed ring based on the newly received encoder packet(s). In this manner, the direction and rate for each toothed ring may be recalculated as each new encoder packet is received.

The system processor of a programmable control system may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations may be performed by circuitry that is specific to a given function.

Those skilled in the art will recognize that the embodiments disclosed herein may have many applications, may be implemented in many manners and, as such, are not to be limited by the preceding exemplary embodiments and examples. Additionally, the functionality of the components of the preceding embodiments may be implemented in different manners. Further, it is to be understood that the steps in the embodiments may be performed in any suitable order, combined into fewer steps or divided into more steps. Thus, the scope of the present invention covers conventionally known and future developed variations and modifications to the system components described herein, as would be understood by those skilled in the art.

What is claimed is:

1. A hoop drive assembly for use with a catheter positioning system, comprising:
   a first toothed ring having a first outer circumference including a first set of outer teeth and a first inner circumference including a first set of inner teeth, wherein the first toothed ring is configured to form a first internal opening surrounded by the first set of inner teeth;
   a second toothed ring having a second outer circumference including a second set of outer teeth, a second inner circumference, and a turret support, wherein the second toothed ring is configured to form a second internal opening defined between the second inner circumference and the turret support and wherein the second toothed ring is aligned with the first toothed ring such that the first toothed ring and the second toothed ring may rotate independently around a common axis of rotation;
   a first gear drive having a first drive shaft surrounded by a first set of drive teeth, wherein the first drive shaft is rotationally coupled to the turret support such that the first drive shaft extends through the first internal opening of the first toothed ring and the first set of drive teeth interlock with the first set of inner teeth of the first toothed ring such that a rotation of the first toothed ring rotates the first drive shaft, and wherein a rotation of the second toothed ring changes an orientation of the turret support relative to the common axis of rotation;
   a first motor coupled to the first set of outer teeth of the first toothed ring and configured to cause the rotation of the first toothed ring; and
   a second motor coupled to the second set of outer teeth of the second toothed ring and configured to cause the rotation of the second toothed ring.

2. The hoop drive assembly of claim 1, further comprising:
   a turret coupled to the turret support, the turret including a first actuator driver interfacing with the first drive shaft, wherein the first actuator driver is configured to move in response to the rotation of the first drive shaft; and
   a modular plate including a first actuator interfacing with the first actuator driver, the first actuator configured to move a first control actuator of a catheter held in the modular plate in response to movement of the first actuator driver.

3. The hoop drive assembly of claim 2, further comprising:
   a third toothed ring having a third outer circumference including a third set of outer teeth and a third inner circumference including a second set of inner teeth, wherein the third toothed ring is configured to form a third internal opening surrounded by the second set of inner teeth, wherein the third toothed ring is aligned with the first toothed ring and second toothed ring such that the first toothed ring, the second toothed ring, and the third toothed ring may rotate independently around the common axis of rotation;
   a second gear drive having a second drive shaft surrounded by a second set of drive teeth, wherein the second drive shaft is rotationally coupled to the turret support such that the second drive shaft extends through the turret support and the first internal opening of the first toothed ring and the second set of drive teeth interlock with the second set of inner teeth of the third toothed ring such that a rotation of the third toothed ring rotates the second drive shaft; and
   a third motor coupled to the third set of outer teeth of the third toothed ring and configured to cause the rotation of the third toothed ring,
   wherein the turret includes a second actuator driver interfacing with the second drive shaft and the second actuator driver is configured to move in response to the rotation of the second drive shaft, and
   wherein the modular plate includes a second actuator interfacing with the second actuator driver, the second actuator configured to move a second control actuator of the catheter held in the modular plate in response to movement of the second actuator driver.

4. The hoop drive assembly of claim 3, wherein the first motor, the second motor, and the third motor are servomotors.

5. The hoop drive assembly of claim 4, wherein:
   the first motor is coupled to the first toothed ring by a first drive belt;
   the second motor is coupled to the second toothed ring by a second drive belt; and
   the third motor is coupled to the third toothed ring by a third drive belt.

6. The hoop drive assembly of claim 4, wherein:
   the first motor is coupled to the first set of outer teeth of the first toothed ring by a first set of one or more drive gears;
   the second motor is coupled to the second set of outer teeth of the second toothed ring by a second set of one or more drive gears; and
   the third motor is coupled to the third set of outer teeth of the third toothed ring by a third set of one or more drive gears.

7. The hoop drive assembly of claim 6, further comprising a drive assembly enclosure encasing at least a portion of the first toothed ring, second toothed ring, third toothed ring, first motor, second motor, and third motor.

8. A catheter positioning system, comprising:
   a linear rail;
   a sled configured to move along the linear rail in response to an actuation of a sled motor;
   a hoop drive assembly coupled to the sled, the hoop drive assembly comprising:
      a first toothed ring having a first outer circumference including a first set of outer teeth and a first inner circumference including a first set of inner teeth, wherein the first toothed ring is configured to form a first internal opening surrounded by the first set of inner teeth;
      a second toothed ring having a second outer circumference including a second set of outer teeth, a second inner circumference, and a turret support, wherein the second toothed ring is configured to form a second internal opening defined between the second inner circumference and the turret support;

a third toothed ring having a third outer circumference including a third set of outer teeth and a third inner circumference including a second set of inner teeth, wherein the third toothed ring is configured to form a third internal opening surrounded by the second set of inner teeth, wherein the third toothed ring is aligned with the first toothed ring and second toothed ring such that the first toothed ring, the second toothed ring, and the third toothed ring may rotate independently around a common axis of rotation;

a first gear drive having a first drive shaft surrounded by a first set of drive teeth, wherein the first drive shaft is rotationally coupled to the turret support such that the first drive shaft extends through the first internal opening of the first toothed ring and the first set of drive teeth interlock with the first set of inner teeth of the first toothed ring such that a rotation of the first toothed ring rotates the first drive shaft, and wherein a rotation of the second toothed ring changes an orientation of the turret support relative to the common axis of rotation;

a second gear drive having a second drive shaft surrounded by a second set of drive teeth, wherein the second drive shaft is rotationally coupled to the turret support such that the second drive shaft extends through the turret support and the first internal opening of the first toothed ring and the second set of drive teeth interlock with the second set of inner teeth of the third toothed ring such that a rotation of the third toothed ring rotates the second drive shaft;

a first motor coupled to the first set of outer teeth of the first toothed ring and configured to cause the rotation of the first toothed ring;

a second motor coupled to the second set of outer teeth of the second toothed ring and configured to cause the rotation of the second toothed ring;

a third motor coupled to the third set of outer teeth of the third toothed ring and configured to cause the rotation of the third toothed ring;

a turret coupled to the turret support, the turret including a first actuator driver interfacing with the first drive shaft and a second actuator driver interfacing with the second drive shaft, wherein the first actuator driver is configured to move in response to the rotation of the first drive shaft and the second actuator driver is configured to move in response to the rotation of the second drive shaft; and a modular plate including a first actuator interfacing with the first actuator driver and a second actuator interfacing with the second actuator driver, wherein the first actuator is configured to move a first control actuator of a catheter held in the modular plate in response to movement of the first actuator driver and the second actuator is configured to move a second control actuator of the catheter held in the modular plate in response to movement of the second actuator driver;

a remote controller; and a system processor connected to the remote controller, the sled motor, the first motor, second motor, and third motor, the system processor configured with processor-executable instructions to perform operations comprising:

activating the sled motor, the first motor, second motor, or third motor in response to an input from the remote controller.

9. The catheter positioning system of claim 8, wherein the first motor, the second motor, and the third motor are servomotors.

10. The catheter positioning system of claim 9, wherein:
the first motor is coupled to the first set of outer teeth of the first toothed ring by a first set of one or more drive gears;
the second motor is coupled to the second set of outer teeth of the second toothed ring by a second set of one or more drive gears; and
the third motor is coupled to the third set of outer teeth of the third toothed ring by a third set of one or more drive gears.

11. The catheter positioning system of claim 10, wherein:
the sled further comprises:
  a sled inductive transmitter; and
  a sled optical receiver;
the turret further comprises:
  a turret inductive receiver;
  a turret optical transmitter; and
  a turret processor connected to the turret inductive receiver, the turret optical transmitter, and the modular plate;
the system processor is configured with processor-executable instructions to perform operations further comprising:
  controlling the sled inductive transmitter to output an inductive signal, which, when received by the turret inductive receiver, provides power to at least the turret processor;
the turret processor is configured with processor-executable instructions to perform operations comprising:
  determining a status associated with the catheter held in the modular plate or the modular plate; and
  outputting an indication of the determined status via the turret optical transmitter; and
the system processor is configured with processor-executable instructions to perform operations further comprising:
  receiving the indication of the determined status via the sled optical receiver; and
  generating a system status indication based at least in part on the indication of the determined status.

12. The catheter positioning system of claim 11, wherein the system processor is configured with processor-executable instructions to perform operations further comprising activating the sled motor, the first motor, second motor, or third motor to align the turret inductive receiver with the sled inductive transmitter and the turret optical transmitter with the sled optical receiver in response to a park position indication.

13. The catheter positioning system of claim 11, wherein the indication of the determined status is one or more of an indication of a catheter type, an indication of a correct modular plate alignment, an indication of an incorrect modular plate alignment, an indication a correct catheter alignment, an indication an incorrect catheter alignment, an indication of a first toothed ring alignment, an indication of a second toothed ring alignment, and an indication of a third toothed ring alignment.

14. The catheter positioning system of claim 10, wherein:
the sled further comprises a sled inductive transceiver;
the turret further comprises:
  a turret inductive transceiver; and a turret processor connected to the turret inductive transceiver and the modular plate;

the system processor is configured with processor-executable instructions to perform operations further comprising controlling the sled inductive transceiver to output an inductive signal, which, when received by the turret inductive transceiver, provides power to at least the turret processor;

the turret processor is configured with processor-executable instructions to perform operations comprising:
 determining a status associated with the catheter held in the modular plate or the modular plate; and
 outputting an indication of the determined status via the turret inductive transceiver; and the system processor is configured with processor-executable instructions to perform operations further comprising:
 receiving the indication of the determined status via the sled inductive transceiver; and
 generating a system status indication based at least in part on the indication of the determined status.

15. The catheter positioning system of claim 14, further comprising a drive assembly enclosure encasing at least a portion of the hoop drive assembly,
 wherein the sled inductive transceiver includes an inductive coil positioned within the drive assembly enclosure at a fourth internal opening of the drive assembly enclosure surrounding a portion of the turret including the turret inductive transceiver, and
 wherein the turret inductive transceiver and the inductive coil of the sled inductive transceiver are aligned such that the inductive signal output from the inductive coil of the sled inductive transceiver can be received by the turret inductive transceiver irrespective of an orientation of the turret within the drive assembly enclosure.

16. The catheter positioning system of claim 15, wherein the indication of the determined status comprises one or more of an indication of a catheter type, an indication of a correct modular plate alignment, an indication of an incorrect modular plate alignment, an indication a correct catheter alignment, an indication an incorrect catheter alignment, an indication of a first toothed ring alignment, an indication of a second toothed ring alignment, and an indication of a third toothed ring alignment.

17. The catheter positioning system of claim 9, wherein:
 the first motor is coupled to the first toothed ring by a first drive belt;
 the second motor is coupled to the second toothed ring by a second drive belt; and
 the third motor is coupled to the third toothed ring by a third drive belt.

18. The catheter positioning system of claim 9, wherein the system processor is configured with processor-executable instructions to perform operations such that one or more of: the first motor, the second motor, and the third motor are activated asynchronously in response to an input from the remote controller.

19. The catheter positioning system of claim 9, wherein the system processor is configured with processor-executable instructions to perform operations such that one or more of: the first motor, the second motor, and the third motor are activated synchronously in response to an input from the remote controller.

20. A catheter positioning system, comprising:
 a linear rail;
 a sled configured to move along the linear rail in response to an actuation of a sled motor;
 a hoop drive assembly coupled to the sled, the hoop drive assembly comprising:
  a first toothed ring having a first outer circumference including a first set of outer teeth and a first inner circumference including a first set of inner teeth, wherein the first toothed ring is configured to form a first internal opening surrounded by the first set of inner teeth;
  a second toothed ring having a second outer circumference including a second set of outer teeth, a second inner circumference, and a turret support, wherein the second toothed ring is configured to form a second internal opening defined between the second inner circumference and the turret support;
  a third toothed ring having a third outer circumference including a third set of outer teeth and a third inner circumference including a second set of inner teeth, wherein the third toothed ring is configured to form a third internal opening surrounded by the second set of inner teeth, wherein the third toothed ring is aligned with the first toothed ring and second toothed ring such that the first toothed ring, the second toothed ring, and the third toothed ring may rotate independently around a common axis of rotation;
  a first gear drive having a first drive shaft surrounded by a first set of drive teeth, wherein the first drive shaft is rotationally coupled to the turret support such that the first drive shaft extends through the first internal opening of the first toothed ring and the first set of drive teeth interlock with the first set of inner teeth of the first toothed ring such that a rotation of the first toothed ring rotates the first drive shaft, and wherein a rotation of the second toothed ring changes an orientation of the turret support relative to the common axis of rotation;
  a second gear drive having a second drive shaft surrounded by a second set of drive teeth, wherein the second drive shaft is rotationally coupled to the turret support such that the second drive shaft extends through the turret support and the first internal opening of the first toothed ring and the second set of drive teeth interlock with the second set of inner teeth of the third toothed ring such that a rotation of the third toothed ring rotates the second drive shaft;
  a turret coupled to the turret support, the turret including a first actuator driver interfacing with the first drive shaft and a second actuator driver interfacing with the second drive shaft, wherein the first actuator driver is configured to move in response to the rotation of the first drive shaft and the second actuator driver is configured to move in response to the rotation of the second drive shaft; and
  a modular plate including a first actuator interfacing with the first actuator driver and a second actuator interfacing with the second actuator driver, wherein the first actuator is configured to move a first control actuator of a catheter held in the modular plate in response to movement of the first actuator driver and the second actuator is configured to move a second control actuator of the catheter held in the modular plate in response to movement of the second actuator driver;
 a first motor coupled to the first set of outer teeth of the first toothed ring via a first motor drive shaft and configured to cause the rotation of the first toothed ring via rotation of the first motor drive shaft;

a second motor coupled to the second set of outer teeth of the second toothed ring via a second motor drive shaft and configured to cause the rotation of the second toothed ring via rotation of the second motor drive shaft;

a third motor coupled to the third set of outer teeth of the third toothed ring via a third motor drive shaft and configured to cause the rotation of the third toothed ring via rotation of the third motor drive shaft;

a remote controller; and a system processor connected to the remote controller, the sled motor, the first motor, second motor, and third motor, the system processor configured with processor-executable instructions to perform operations comprising:

activating the sled motor, the first motor, second motor, or third motor in response to an input from the remote controller.

21. The catheter positioning system of claim 20, wherein the first motor drive shaft, second motor drive shaft, and third motor drive shaft are flexible drive shafts.

22. The catheter positioning system of claim 20, wherein the first motor drive shaft, second motor drive shaft, and third motor drive shaft are located within the linear rail.

23. The catheter positioning system of claim 20, wherein:

the rotation of the first motor drive shaft is transferred to the first toothed ring at least in part by a first drive belt;

the rotation of the second motor drive shaft is transferred to the second toothed ring at least in part by a second drive belt; and the rotation of the third motor drive shaft is transferred to the third toothed ring at least in part by a third drive belt.

24. The catheter positioning system of claim 23, wherein:

the rotation of the first motor drive shaft about a first motor drive shaft axis is translated to rotation of the first toothed ring about a common toothed ring axis at least in part by a first interface gear and the first drive belt;

the rotation of the second motor drive shaft about a second motor drive shaft axis is translated to rotation of the second toothed ring about the common toothed ring axis at least in part by a second interface gear and the second drive belt; and the rotation of the third motor drive shaft about a third motor drive shaft axis is translated to rotation of the third toothed ring about the common toothed ring axis at least in part by a third interface gear and the third drive belt.

25. The catheter positioning system of claim 23, wherein:

the rotation of the first motor drive shaft about a first motor drive shaft axis is translated to rotation of the first toothed ring about a common toothed ring axis at least in part by a first flexible interface gear and the first drive belt, wherein the first flexible interface gear and a first flexible drive gear driven by the first motor drive shaft about the first motor drive shaft axis are coupled in flexible relation;

the rotation of the second motor drive shaft about a second motor drive shaft axis is translated to rotation of the second toothed ring about the common toothed ring axis at least in part by a second flexible interface gear and the second drive belt, wherein the second flexible interface gear and a second flexible drive gear driven by the second motor drive shaft about the second motor drive shaft axis are coupled in flexible relation; and the rotation of the third motor drive shaft about a third motor drive shaft axis is translated to rotation of the third toothed ring about the common toothed ring axis at least in part by a third flexible interface gear and the third drive belt, wherein the third flexible interface gear and a third flexible drive gear driven by the third motor drive shaft about the third motor drive shaft axis are coupled in flexible relation.

* * * * *